United States Patent
Arnold et al.

(10) Patent No.: US 10,174,352 B2
(45) Date of Patent: Jan. 8, 2019

(54) METHODS FOR AMPLIFICATION OF NUCLEIC ACIDS ON SOLID SUPPORT

(71) Applicants: Lyle J. Arnold, Poway, CA (US); Norman C. Nelson, San Diego, CA (US)

(72) Inventors: Lyle J. Arnold, Poway, CA (US); Norman C. Nelson, San Diego, CA (US)

(73) Assignee: AEGEA BIOTECHNOLOGIES, INC.

( * ) Notice: Subject to any disclaimer, the term of this patent is extended or adjusted under 35 U.S.C. 154(b) by 323 days.

(21) Appl. No.: 14/773,362

(22) PCT Filed: Mar. 14, 2014

(86) PCT No.: PCT/US2014/029817
§ 371 (c)(1),
(2) Date: Sep. 7, 2015

(87) PCT Pub. No.: WO2014/153260
PCT Pub. Date: Sep. 25, 2014

(65) Prior Publication Data
US 2016/0017392 A1   Jan. 21, 2016

Related U.S. Application Data

(60) Provisional application No. 61/781,356, filed on Mar. 14, 2013.

(51) Int. Cl.
*C12Q 1/68*     (2018.01)
*C12P 19/34*    (2006.01)
(Continued)

(52) U.S. Cl.
CPC ............ *C12P 19/34* (2013.01); *C12Q 1/6853* (2013.01); *C12Q 1/6865* (2013.01)

(58) Field of Classification Search
CPC ........ C12Q 2525/186; C12Q 2565/515; C12Q 1/6853; C12Q 1/6865; C12Q 2531/143;
(Continued)

(56) References Cited

U.S. PATENT DOCUMENTS

| | | | |
|---|---|---|---|
| 5,399,491 A * | 3/1995 | Kacian | C12Q 1/6855 435/6.1 |
| 2005/0064432 A1* | 3/2005 | Huang | C12Q 1/6865 435/6.12 |

(Continued)

OTHER PUBLICATIONS

Linnen, J.M. et al., Sensitive detection of genetic variants of HIV-1 and HCV with an HIV-1/HCV assay based on transcription-mediated amplification, J. Virol. Meth., vol. 102, pp. 139-155 (Year: 2002).*

(Continued)

*Primary Examiner* — Teresa E Strzelecka
(74) *Attorney, Agent, or Firm* — David B. Waller

(57) ABSTRACT

The present invention provides methods for amplifying a nucleic acid from a sample containing a mixture of nucleic acids utilizing a solid support. Methods are provided utilizing user-defined primer oligonucleotides for directional amplification that assists in further manipulation of the target nucleic acid, such as sequencing. Methods are also provided utilizing blocker and displacer oligonucleotides for generating amplified target nucleic acids of defined length. One of these methods provides a first oligonucleotide and a second oligonucleotide affixed to a solid support or separate solid supports. The first oligonucleotide is blocked to prevent extension from the 3'-terminus and has a sequence complementary to a first portion of a target nucleic acid. The second oligonucleotide has a sequence that is identical to a second portion of the target nucleic acid. In this method, a sample is applied to the solid support and the target nucleic acid within the sample binds said first oligonucleotide. The (Continued)

solid support is then washed to remove unbound nucleic acids. A primer sequence containing a target binding region and a polymerase promoter sequence is then annealed to the bound target nucleic acid and extended producing a first duplex nucleic acid. The target sequence is then removed leaving a first nucleic acid that can now bind the second oligonucleotide. The second oligonucleotide is extended to produce a second duplex nucleic acid that contains a second nucleic acid. The second nucleic acid is then amplified by adding a polymerase.

4 Claims, 15 Drawing Sheets

(51) Int. Cl.
*C12Q 1/6853* (2018.01)
*C12Q 1/6865* (2018.01)
*C07H 21/02* (2006.01)

(58) Field of Classification Search
CPC ........ C12Q 2533/101; C12Q 2565/537; C12P 19/34
See application file for complete search history.

(56) References Cited

U.S. PATENT DOCUMENTS

2008/0108055 A1* 5/2008 Linnen .................. C12Q 1/701
435/5
2009/0253123 A1* 10/2009 Chan ..................... C12Q 1/706
435/5

OTHER PUBLICATIONS

Pastinen, T. et al., A System for Specific, High-throughput Genotyping by Allele-specific Primer Extension on Microarrays, Genome Res., vol. 10, pp. 1031-1042 (Year: 2000).*
Andreadis, J.D. et al., A System for Specific, High-throughput Genotyping by Allele-specific Primer Extension on Microarrays, Nucl. Acids Res., vol. 28, e5, pp. 1-8 (Year: 2000).*

* cited by examiner

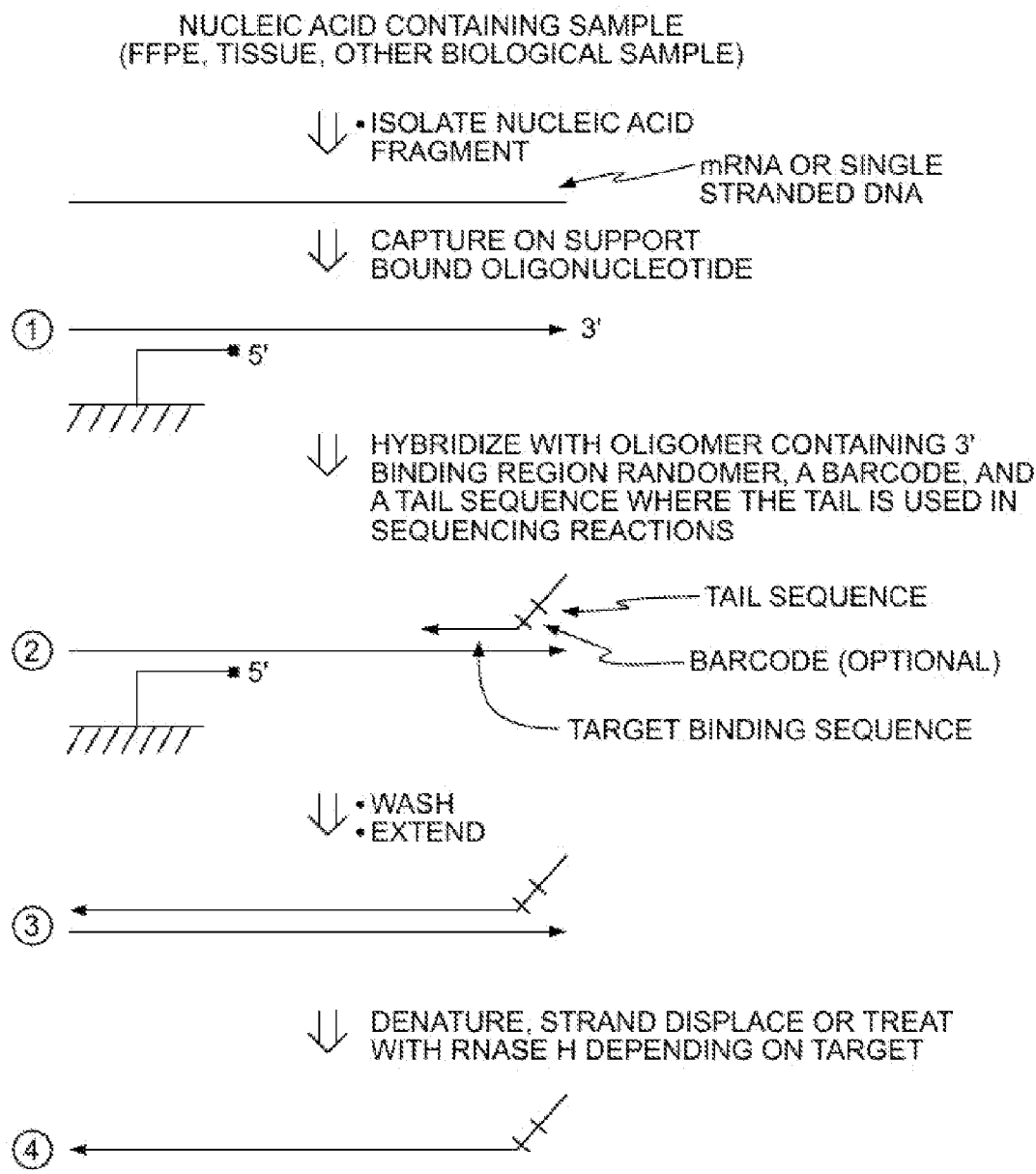

OPTIONS:

- IN STEP ②THE PRIMING SEQUENCE MAY BE A DUPLEX OR A HAIRPIN WITH AN OPTIONAL LIGATION STEP TO ATTACH THE PRIMER DIRECTLY TO THE 3' END OF THE TARGET SEQUENCE

METHODS FOR AMPLIFICATION OF NUCLEIC ACIDS ON SOLID SUPPORT

CROSS-REFERENCE TO RELATED APPLICATIONS

This application is a non-provisional patent application of provisional patent application Ser. No. 61/781,356 filed Mar. 14, 2013 and claims the benefit of the filing date of PCT/US2014/029817 filed 14 Mar. 2014 under 35 U.S.C. § 371 from which the PCT application claims priority.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION (1) Field of the Invention

The present invention relates to methods of purification, immobilization and amplification of nucleic acids. Specifically, nucleic acid amplification using a solid support.

(2) Description of Related Art

There are a variety of methods for the purification and amplification of nucleic acids known to those skilled in the art. However, these methods can be slow, tedious, expensive and difficult to automate and manufacture. They also lack the performance in regards to sensitivity, specificity, precision, accuracy and other features that would otherwise allow them to be used successfully in a number of diverse applications. These methods are often complicated, requiring isolation of nucleic acid targets from samples, preparing the targets for amplification, performing amplification and detecting the amplification product. In some applications, this may also include preparing templates for sequencing including next generation sequencing and sequencing the target nucleic acids. In many of these methods one or more purification steps may also be required. All of these steps increase performance time, cost, complexity and labor. Providing methods with versatility as to specificity, sensitivity, selectivity, precision and accuracy is important. As are methods that are rapid, efficient and easy to use with minimal assay steps and reagents for readily obtaining a desired isolated and amplified product from a raw sample. These products may be amplified nucleic acids or set of amplified nucleic acids (i.e., multiplexing, including high level multiplexing) that may be utilized as templates, free in solution or on solid supports, for immediate sequencing and next generation sequencing. In addition, methods for directional amplification that preserve strand orientation provide proper alignment of sequences during mapping and more accurate quantitative determinations (e.g. of gene expression levels). In addition, these methods can be utilized with a wide variety of nucleic acid amplification methods that are known in the art. In addition these methods can be utilized with tag sequences. The present invention provides methods for purifying, immobilizing and amplifying specific nucleic acids from a sample that overcome many of the current limitations in the art.

BRIEF SUMMARY OF THE INVENTION

The present invention provides methods of immobilizing and amplifying nucleic acids on solid support. More specifically, it is a method of immobilizing and amplifying a desired nucleic acid or a number of nucleic acids (multiplexing) from a sample containing a mixture of nucleic acids.

In one aspect of the present invention, the method provides first and second oligonucleotides affixed to a solid support or alternatively separate solid supports. The first oligonucleotide is blocked to prevent extension from the 3'-terminus and has a sequence complementary to a first portion of a target nucleic acid. The second oligonucleotide has a sequence that is identical to a second portion of the target nucleic acid. A sample is applied to the solid support and target sequences in the sample bind the first oligonucleotide. The solid support is then washed to remove unbound nucleic acids and other components from the sample. A primer containing a target-binding region and a tag region comprising polymerase promoter sequence is annealed to the bound target nucleic acid. The primer is extended by polymerase to produce a first duplex nucleic acid. The target sequence is removed from the first duplex nucleic acid to produce an unbound first nucleic acid. The first nucleic acid is annealed to the second oligonucleotide and the second oligonucleotide is extended by polymerase to produce a second duplex nucleic acid containing a first nucleic acid and a second nucleic acid. Multiple copies of a third nucleic acid are then generated by adding polymerase specific to the promoter sequence to the solid support thereby amplifying the target nucleic acid.

In a second embodiment the primer may be combined with the sample and solid support such that the primer hybridizes to the target and the target hybridizes to the first oligonucleotide concurrently. The solid support is then washed to remove unbound nucleic acids and primer as well as other components from the sample.

In a third embodiment, the method may further comprise steps that allow for additional amplification of the desired target nucleic acid. In these steps, the multiple copies of the third nucleic acid bind to the second oligonucleotide on the solid support. The second oligonucleotide is extended by polymerase to produce a third duplex nucleic acid. The third nucleic acid is removed from the third duplex nucleic acid to produce a fourth nucleic acid bound to the solid support. The primer sequence is annealed to the fourth nucleic acid and both the primer and the fourth nucleic acid are extended by polymerase to produce a fourth-duplex nucleic acid containing a fifth nucleic acid and additional second nucleic acid. The fourth duplex nucleic acid is incubated with a polymerase being specific to a promoter on the fourth duplex nucleic acid to produce additional multiple copies of the third nucleic acid. According to this embodiment the third nucleic acid may then be amplified further.

In a fourth embodiment, the primer comprises a tag sequence containing one or more non-natural nucleotides, such as isocytosine (isoC) and/or isoguanine (isoG) to increase specificity for binding the target nucleic acid and decreases amplification of other nucleic acids.

In a fifth embodiment, four different second oligonucleotides may be bound to the solid support each having a different nucleotide at the 3'-terminus and sequence that binds the first nucleic acid at a specific single nucleotide polymorphism (SNP) site. In this configuration, amplification may be utilized to identify all four possible SNPs in a single assay.

In a second aspect, directional amplification of a fragmented nucleic acid target is provided for subsequent manipulation, such as sequencing. In one embodiment, a sample and a first primer are applied to a solid support. The first primer comprises a random sequence of about 6 to about 9 nucleotides on the 3'-terminus and a first tag sequence on the 5'-terminus, which is used to determine the orientation of the fragmented nucleic acid target. First and second oligonucleotides bound to solid support are provided that may be bound to the same solid support or alternatively on different solid supports. The first oligonucleotide is optionally blocked to prevent potential exonuclease digestion, for example, at the 5'-terminus and has a sequence complementary to a portion of the fragmented nucleic acid target. Alternatively, the first oligonucleotide comprises a sequence (such as for example, a random or semi-random sequence) that allows for immobilization of a number of fragments from the fragmented nucleic acid target. The second oligonucleotide sequence is complementary to at least a portion of said tag sequence of the first primer.

The first primer is annealed to the fragmented nucleic acid target and the bound fragmented nucleic acid target is annealed to the first oligonucleotide. The solid support is washed to remove unbound sample and first primer. The first primer sequence is extended by polymerase to produce a first duplex nucleic acid containing the fragmented nucleic acid target and a first nucleic acid.

The fragmented nucleic acid target is removed from the first duplex nucleic acid to produce a first nucleic acid. The first nucleic acid is annealed to the second oligonucleotide and a second primer is added to the solid support. The second primer comprises a random sequence of about 6 to about 9 nucleotides on the 3'-terminus and a second tag sequence on the 5'-terminus, which may or may not contain elements the same as or similar to those found in the first tag sequence of the first primer. The second primer is annealed to the first nucleic acid and extended by polymerase to produce a second duplex containing the first nucleic acid and a second nucleic acid having a first tag sequence on the 3'-terminus and a second tag sequence on the 5'-terminus.

This second nucleic acid is further amplified to produce a target nucleic acid containing tag sequences that determine the orientation of the nucleic acid target.

In one embodiment of this aspect, the first primer may further comprise a barcode sequence as part of the tag sequence to further assist in identification and orientation.

In third aspect, a method is provided wherein the first primer having a sequence is complementary to a first portion of the target nucleic acid is immobilized on a solid support. In one embodiment, displacer and blocker oligonucleotides are utilized. The displacer oligonucleotide hybridizes to the nucleic acid target at a location in the target sequence that is 3' of another bound oligonucleotide or oligonucleotides on the same nucleic acid target. When the displacer is extended with polymerase, the growing extension product encounters the other bound oligonucleotide(s) and displaces it/them, along with any extension product(s) initiated by the bound oligonucleotide(s), from the target nucleic acid strand. In this embodiment, the displacer oligonucleotide has a sequence complementary to a second portion of the target nucleic acid that is located to the 3' side of the first portion. The blocker has an oligonucleotide sequence complementary to a third portion of the target nucleic acid sequence that is located to the 5' side of the first portion. These oligonucleotides and the target nucleic acid are applied to the solid support. The displacer and blocker oligonucleotides are annealed to the target nucleic acid and the annealed target is immobilized onto the solid support by hybridization to the first primer.

The solid support is washed to remove unbound nucleic acids and other components of the sample. The first primer is extended by polymerase. Extension terminates at the blocker oligonucleotide to produce a first duplex nucleic acid of defined length. The displacer oligonucleotide is also extended by polymerase to displace the target strand from the first duplex nucleic acid. Extension terminates at the blocker oligonucleotide to produce a second duplex nucleic acid containing a second nucleic acid of defined length unbound to the solid support.

A second primer is annealed to the first nucleic acid and extended by polymerase to produce a third duplex containing the first nucleic acid and a third nucleic acid. The second and third duplex nucleic acids are then dissociated, e.g., heat denaturation or other appropriate means known in the art. The second primer is annealed to the first nucleic acid and extended to produce more of the third duplex nucleic acid.

The third nucleic acid is immobilized onto the solid support by hybridization to unoccupied first primer. The first primer is extended by polymerase to produce more third duplex nucleic acid. The original target nucleic acid, with displacer and blocker oligonucleotides bound thereto, is annealed to unoccupied first primer on the solid support. The first primer is extended by polymerase to produce more first duplex nucleic acid. The displacer oligonucleotide is also extended, displacing the target nucleic acid from the first duplex nucleic acid. Extension terminates at the blocker oligonucleotide to produce a second duplex nucleic acid containing a second nucleic acid of defined length that is not bound to the support.

The second primer is annealed to the second nucleic acid by hybridization and is extended by polymerase to produce a fourth duplex nucleic acid containing the second nucleic acid and a fourth nucleic acid. All duplexes are then denatured, and the cycle is repeated as desired to amplify the target nucleic acid.

In one embodiment of this aspect, the nucleic acid target is double stranded and both strands are immobilized and amplified. A primer and optionally a displacer and/or a blocker are prepared for each strand according to the method described above. The primer for each target nucleic acid strand is affixed to a solid support if a single support is utilized or one primer on each support if two supports are utilized. Each target strand is immobilized by hybridization to the primer having a complementary sequence for that target nucleic acid strand. The primer is extended by polymerase to produce a cDNA and the target nucleic acid strands are then removed. Removal may be by displacement if a displacer is used, by heat denaturation if a displacer is not used, or by some other appropriate method known in the art. At this point, the primer designed for one of the target nucleic acid strands can serve as the second primer for the cDNA produced from the other target nucleic acid strand, and vice versa. The cDNAs bind to their respective second primers (i.e., the first primers of the opposite target nucleic acid strands), the second primers are extended by polymerase and the resulting duplexes are disassociated. This process is then repeated as desired thereby amplifying the target nucleic acid.

Other aspects of the invention are found throughout the specification.

DETAILED DESCRIPTION OF THE INVENTION

Figure 1A:
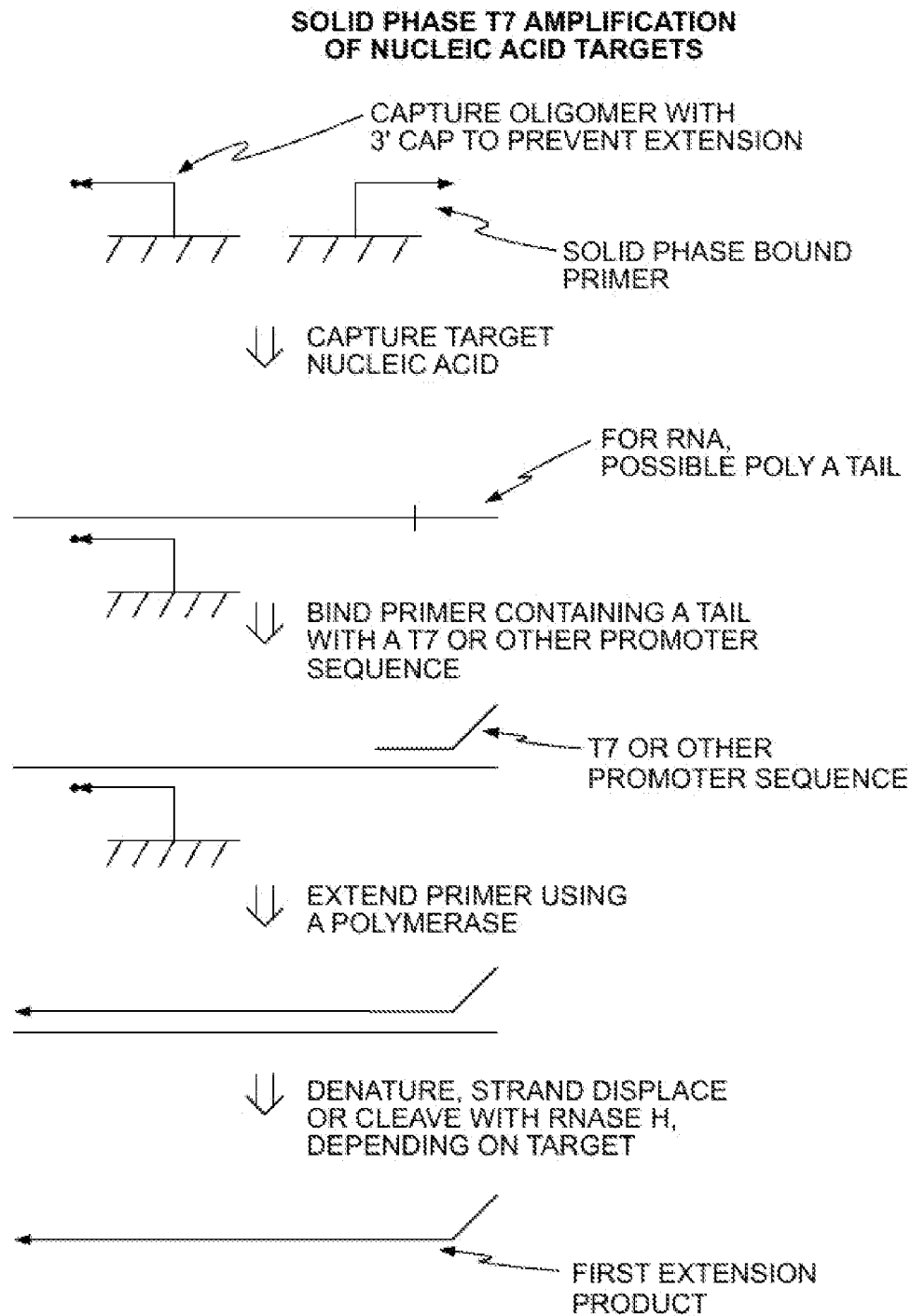
FIG. 1: (A) is a schematic diagram of one method of the present invention and (B) shows additional steps that may be incorporated into the method in FIG. 1A.
Figure 1A:
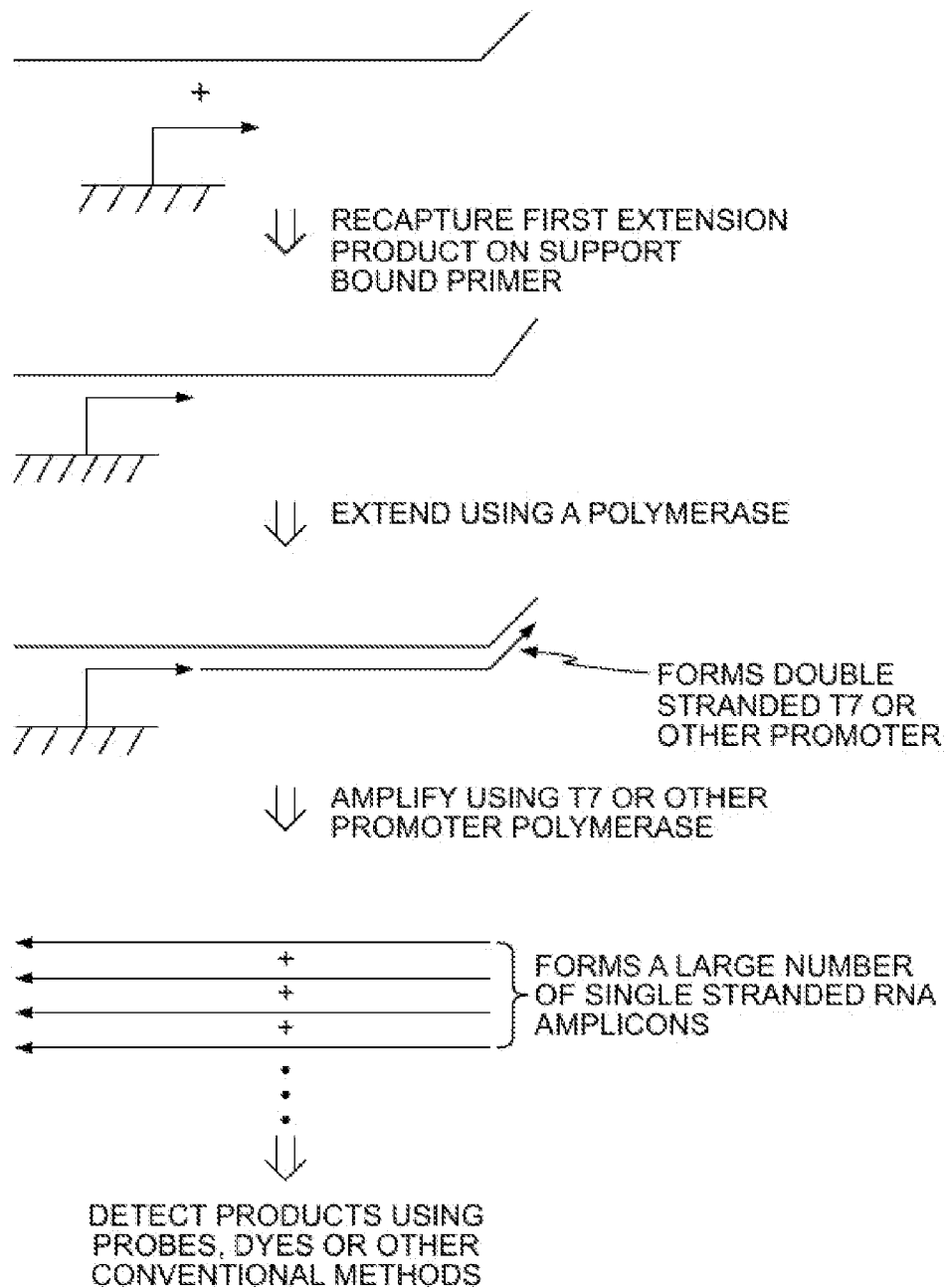
Figure 1B:
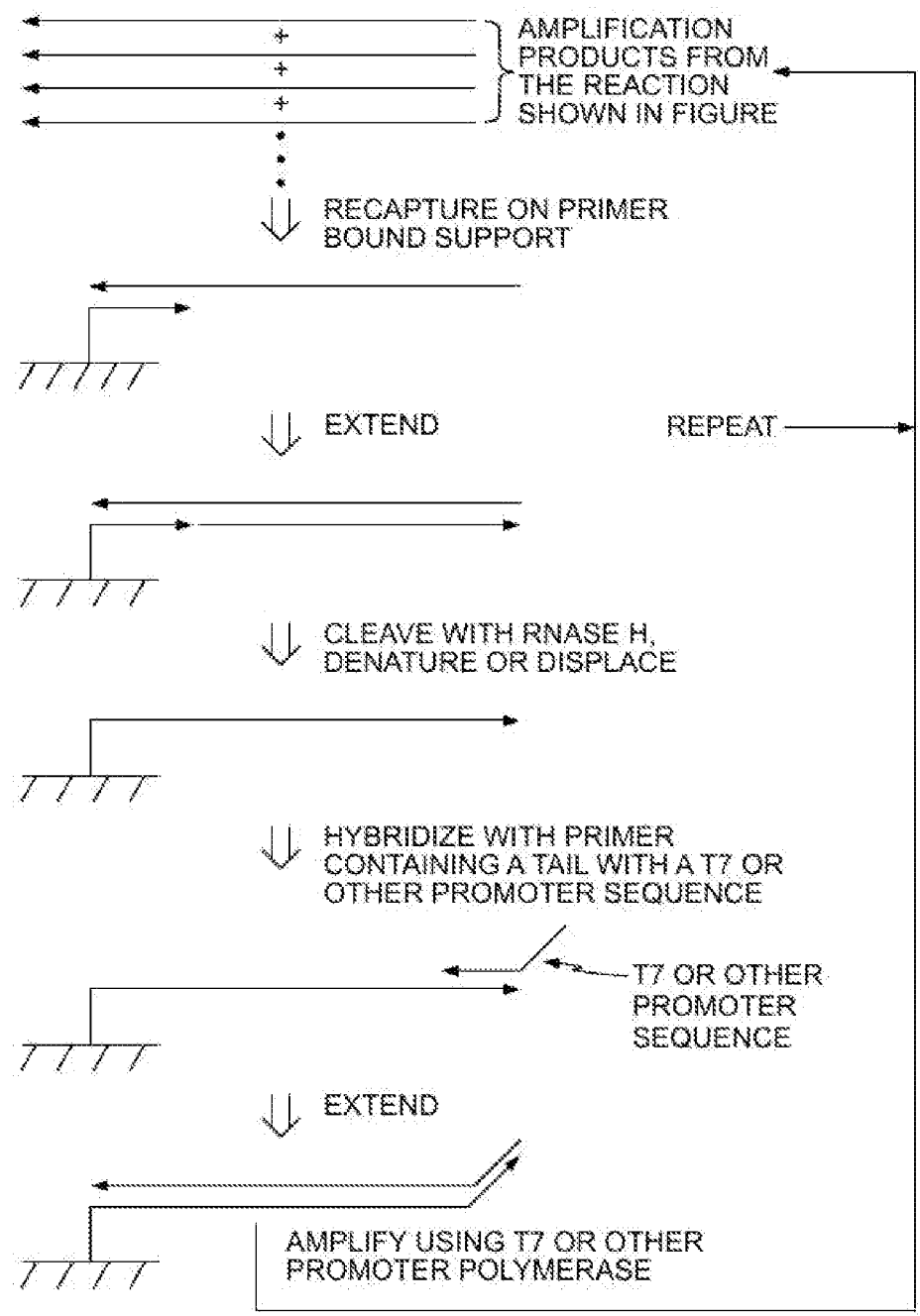

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "oligonucleotide" as used herein refers to a polymeric form of nucleotides, either ribonucleotides or deoxyribonucleotides, incorporating natural and non-natural nucleotides of a length ranging from at least 2, or generally about 5 to about 200, or more commonly to about 100. Thus, this term includes double- and single-stranded DNA and RNA. In addition, oligonucleotides may be nuclease resistant and include but are not limited to 2'-O-methyl ribonucleotides, phosphorothioate nucleotides, phosphorodithioate nucleotides, phosphoramidate nucleotides, and methylphosphonate nucleotides.

The term "target," "target sequence," or "target nucleic acid" as used herein refers to a nucleic acid that contains a polynucleotide sequence of interest, for which purification, isolation, capture, immobilization, amplification, identification, detection, quantitation, mass determination and/or sequencing, and the like is/are desired. The target sequence may be known or not known, in terms of its actual sequence.

The term "primer" or "primer sequence" as used herein are nucleic acids comprising sequences selected to be substantially complementary to each specific sequence to be amplified. More specifically, primers are sufficiently complementary to hybridize to their respective targets. Therefore, the primer sequence need not reflect the exact sequence of the target. Non-complementary bases or longer sequences can be interspersed into the primer, provided that the primer sequence has sufficient complementarity with the sequence of the target nucleic acid to permit hybridization and extension.

In addition, primers may be nuclease resistant and include primers that have been modified to prevent degradation by exonucleases. In some embodiments, the primers have been modified to protect against 3' or 5' exonuclease activity. Such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the primer(s) and/or probe(s) employed in an amplification reaction are protected against 3' and/or 5' exonuclease activity by one or more modifications.

The skilled artisan is capable of designing and preparing primers that are appropriate for extension of a target sequence. The length of primers for use in the methods and compositions provided herein depends on several factors including the nucleotide sequence identity and the temperature at which these nucleic acids are hybridized or used during in vitro nucleic acid extension. The considerations necessary to determine a preferred length for the primer of a particular sequence identity are well known to the person of ordinary skill.

The term "support" or "solid support" refers to conventional supports that include, for example, polymers such as microtiter wells, beads, particles or fibers, and silane or silicate supports such as glass slides or tubes to which capture molecules such as the first and second oligonucleotides are covalently or non-covalently bound.

The term "sample" as used herein refers to essentially any sample containing the desired target nucleic acid(s), including but not limited to tissue or fluid isolated from a human being or an animal, including but not limited to, for example, blood, plasma, serum, spinal fluid, lymph fluid, tears or saliva, urine, semen, stool, sputum, vomit, stomach aspirates, bronchial aspirates, swabs (nasopharyngeal, rectal, ocular, urogenital, etc.), organs, muscle, bone marrow, FFPE tissue, skin, tumors and/or cells obtained from any part of the organism; plant material, cells, fluid, etc.; an individual bacterium, groups of bacteria and cultures thereof; food; cosmetics; drugs/pharmaceuticals; materials prepared via bioprocessing (finished product as well as intermediate materials); water; environmental samples, including but not limited to, for example, soil, water and air; semi-purified or purified nucleic acids from the sources listed above, for example; nucleic acids that are the result of a process, such as template formation for sequencing, including next generation sequencing, sample processing, nuclease digestion, restriction enzyme digestion, replication, and the like.

The term "amplifying" or "amplification" as used herein refers to the process of creating nucleic acid strands that are identical or complementary to a complete target nucleic acid sequence, or a portion thereof, or a universal sequence that serves as a surrogate for the target nucleic acid sequence. The term "identical" as used herein refers to a nucleic acid having the same or substantially the same nucleotide sequence as another nucleic acid.

The term "affixed" as used herein refers to the attachment of a molecule(s), such as the first and second oligonucleotides, to a solid support. A wide variety of methods commonly known in the art can be used for attachment. One preferred method is covalent attachment.

The term "nucleic acid" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions.

Nitrogenous bases may be conventional bases (A, G, C, T, U), non-natural nucleotides such as isocytosine and isoguanine, analogs thereof (e.g., inosine; The Biochemistry of the Nucleic Acids 5-36, Adams et al., ed., 11th ed., 1992), derivatives of purine or pyrimidine bases (e.g., $N^4$-methyl deoxyguanosine, deaza- or aza-purines, deaza- or aza-pyrimidines, pyrimidines or purines with altered or replacement substituent groups at any of a variety of chemical positions, e.g., 2-amino-6-methylaminopurine, $O^6$-methyl-guanine, 4-thio-pyrimidines, 4-amino-pyrimidines, 4-dimethylhydrazine-pyrimidines, and $O^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121).

Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, Biochemistry 43(42):13233-41).

The term "releasing" or "released" as used herein refers to separating the desired amplified nucleic acid from its template by heating the duplex to a temperature that denatures the nucleic acid duplex forming two separate oligonucleotide strands.

The term "removing" as used herein refers to a variety of methods used to isolate or otherwise remove and separate one nucleic acid strand of a duplex from another, such as for example enzymatic, thermal and/or chemical digestion, degradation and/or cleavage of one of the strands of the duplex, or denaturation/dissociation of the strands by heat, acoustic energy, chemicals, enzymes or a combination thereof.

The terms "tag region" or "tag sequence" refer to a user-defined nucleic acid sequence or sequences that are incorporated into an oligonucleotide or other nucleic acid structure, such as a primer, to provide one or more desired functionalities. Examples of such elements include, for example, adapters, sequencing primers, amplification primers, capture and/or anchor elements, hybridization sites, promoter elements, restriction endonuclease site, detection elements, mass tags, barcodes, binding elements, and/or non-natural nucleotides. Other elements include those that clearly differentiate and/or identify one or more nucleic acids or nucleic acid fragments in which a tag sequence has been incorporated from other nucleic acids or nucleic acid fragments in a mixture, elements that are unique in a mixture of nucleic acids so as to minimize cross reactivity and the like and elements to aid in the determination of sequence orientation. Some or all of the elements in a tag sequence can be incorporated into amplification products.

The term "hybridization," "hybridize," "anneal" or "annealing" as used herein refers to the ability, under the appropriate conditions, for nucleic acids having substantial complementary sequences to bind to one another by Watson & Crick base pairing. Nucleic acid annealing or hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994). The term "substantial complementary" as used herein refers both to complete complementarity of binding nucleic acids, as well as complementarity sufficient to achieve the desired binding of nucleic acids. Correspondingly, the term "complementary hybrids" encompasses substantially complementary hybrids.

The term "displacer oligonucleotide" or "displacer" as used herein refers to an oligonucleotide that hybridizes to a nucleic acid target at a location in the target sequence that is 3' of another bound oligonucleotide or oligonucleotides on the same nucleic acid target. When the displacer is extended with polymerase, the growing extension product encounters the other bound oligonucleotide(s) and displaces it/them, along with any extension product(s) initiated by the bound oligonucleotide(s), from the nucleic acid strand.

The term "blocker oligonucleotide" or "blocker" as used herein refers to a modified oligonucleotide or agent that binds to a nucleic acid or agent that binds to a modified nucleic acid that is capable of preventing or inhibiting replication and is incorporated into the primer(s) and/or probe(s) in an amplification reaction. Blocker oligonucleotides may include 2' fluoro (2'-deoxy-2'-fluoro-nucleosides) modifications, nuclease resistant nucleotides, or nucleotides with 3'-modifications all of which inhibit or prevent replication.

General methods for amplifying nucleic acid sequences have been well described and are well known in the art. Any such methods can be employed with the methods of the present invention. In some embodiments, the amplification uses digital PCR methods, such as those described, for example, in Vogelstein and Kinzler ("Digital PCR," *PNAS*, 96:9236-9241 (1999); incorporated by reference herein in its entirety). Such methods include diluting the sample containing the target region prior to amplification of the target region. Dilution can include dilution into conventional plates, multiwell plates, nanowells, as well as dilution onto micropads or as microdroplets. (See, e.g., Beer N R, et al., "On-chip, real time, single copy polymerase chain reaction in picoliter droplets," *Anal. Chem.* 79(22):8471-8475 (2007); Vogelstein and Kinzler, "Digital PCR," *PNAS*, 96:9236-9241 (1999); and Pohl and Shih, "Principle and applications of digital PCR," *Expert Review of Molecular Diagnostics*, 4(1):41-47 (2004); all of which are incorporated by reference herein in their entirety.) In some embodiments, the amplification is by digital PCR.

In some cases, the enzymes employed with the methods of the present invention for amplification of the target region include but are not limited to high-fidelity DNA polymerases, for example DNA polymerases that have 3'-5' exonuclease proof-reading capabilities. Examples of enzymes that can be used with the methods include but are not limited to AmpliTaq, Phusion HS II, Deep Vent, and Kapa HiFi DNA polymerase.

High-fidelity enzymes allow for high-fidelity (highly accurate) amplification of a target sequence. In some embodiments, the enzymes employed will include high-fidelity DNA polymerases, for example DNA polymerases that have 3'-5' exonuclease proof-reading capabilities. Enzymes that can be used with the methods include but are not limited to AmpliTaq, Phusion HS II, Deep Vent, and Kapa HiFi DNA polymerase.

The amplification product can be detected/analyzed using a number of methods known to those skilled in the art including, but not limited to, fluorescence, electrochemical detection, gel analysis and sequencing. Furthermore, the product can be quantitated using a number of methods known to those skilled in the art such as real time amplification. Quantitation can be normalized by comparison to so-called "house-keeping genes" such as actin or GAPDH or to an internal control that can be added to the reaction in a known amount. Such methods are well known and have been described in Sambrook and Russell, *Molecular Cloning: A Laboratory Manual* (3rd Ed.) (2001).

Instrumentation for performing the methods described herein is readily available. Such instruments can include instruments for real-time and end-point PCR assays, emulsion PCR, solid-phase PCR, melting curve analyses, and sequencing analyses. Such instruments include Life Technologies 7500 Fast Dx real-time instrument (which is also capable of high-resolution melting curve analyses) and the 3500 xl capillary gel instruments. Other instruments known in the art to be useful in the methods of the present invention are also contemplated for use by one of skill in the art in practicing the methods of the present invention.

The present invention provides methods for immobilization and amplification of a nucleic acid target from a sample containing a mixture of nucleic acids. A variety of amplification techniques are known in the art. Some of these known methods may be utilized with the methods of the present invention. Patent application publication no.: 2011/0003305 A1 discloses some of these methods and is incorporate by reference herein in its entirety.

The methods of the invention utilize a variety of nucleic acid structures and compositions. Synthesis of these oligonucleotides was performed using standard phosphoramidite chemistry well known to those skilled in the art.

One method of the present invention, shown in FIG. 1A, provides first and second immobilization oligonucleotides bound to either the same or adjacent regions of a solid support or alternatively to different supports. The sequence of the first immobilization oligonucleotide is complementary to a first portion of the target nucleic acid sequence. The sequence of the second immobilization oligonucleotide is identical to a second portion of the target nucleic acid sequence. The 3'-terminus of the first immobilization oligonucleotide is blocked in a manner preventing extension whereas the 3'-terminus of the second immobilization oligonucleotide allows for extension.

The 3'-terminus of an oligonucleotide can be chemically or structurally blocked using a blocking moiety, as is generally known in the art. Blocked oligonucleotides are described in, e.g., U.S. Pat. Nos. 5,399,491, 5,554,516, 5,824,518, and U.S. App. No. 2006-0046265. A blocked oligonucleotide refers to an oligonucleotide that includes a chemical and/or structural modification that is usually near or at the 3'-terminus and that prevents or impedes initiation of DNA synthesis from the oligonucleotide by enzymatic means. Examples of such modifications include use of a 3'2'-dideoxynucleotide base, a 3'-non-nucleotide moiety that prevents enzymatic extension, or attachment of a short sequence in 3'- to 5'-orientation to the oligonucleotide to make a final oligonucleotide with two 5'-termini (i.e., a first 5'- to 3'-oligonucleotide attached to a second, usually shorter, 5'- to 3'-oligonucleotide by covalently joining the oligonucleotides at their 3'-termini). Another example of a modification is a "cap" made up of a sequence that is complementary to at least 3 nucleotides at the 3'-terminus of the oligonucleotide such that the 5'-terminal base of the cap is complementary to the 3'-terminal base of the oligonucleotide. In addition, blocking extension of an oligonucleotide can be achieved by tethering its 3'-terminus to a solid support. Thus, the immobilization oligonucleotide(s) used in the present invention may be oriented such that it is attached to a solid support(s) at or near its 3'-terminus if blocking of extension is desired.

The first portion and second portion of the target nucleic acid sequence may be the same or different. Under the majority of circumstances, it is preferable that the first and second immobilization oligonucleotide sequences are not exactly complementary.

In one example, an RNA target (e.g., mRNA) from a sample is immobilized onto the solid support by hybridization to the first immobilization oligonucleotide. This may be a first solid support if the first and second immobilization oligonucleotides are bound to different supports. The solid support is washed to remove unbound components of the sample. Next, a first primer comprising a target-binding region and a tag region, the tag region comprising a polymerase promoter sequence (e.g. T7 RNA polymerase promoter sequence), is hybridized to the immobilized target RNA. The first primer is then extended using a polymerase enzyme to produce a first cDNA strand bound to a segment of the RNA target. The segment of RNA target is then enzymatically degraded (e.g. RNaseH), leaving the first cDNA strand free in solution. The first cDNA strand then anneals to the second immobilization oligonucleotide on the first solid support, or on a second solid support if the first and second immobilization oligonucleotides are bound to different supports. The second immobilization oligonucleotide is then extended using a polymerase enzyme to produce a second cDNA strand bound to a segment of the first cDNA strand. This creates a duplex, which includes an active double stranded T7 RNA polymerase promoter site. Multiple RNA transcripts are then generated in solution from this duplex using a T7 RNA polymerase.

Alternatively, the first immobilization oligonucleotide may be used to stop the extension of the first primer in this method. Thus, if desired, the length of the first cDNA strand can be determined by location of the first immobilization oligonucleotide on the target strand. For example, this blocking property can be effectuated, by designing the target-binding region of the immobilization oligonucleotide to have very high affinity for the target nucleic acid, such as equipping it with 2'-methoxy residues if the target nucleic acid is RNA or locked nucleic acids (LNAs) if the target is DNA, or by attaching a blocking group (e.g. steric blocker, intercalating molecule or groove binder) at the 5'-terminus to arrest progress of the polymerase. This technique may also be utilized in other methods of the present invention.

In one embodiment, the first and second immobilization oligonucleotides may be configured on a solid support or supports in a wide variety of ways, including but not limited to, binding both oligonucleotides to the same solid support. This includes binding the immobilization oligonucleotides to essentially the entire surface, or binding the immobilization oligonucleotides to specific areas on the surface, such as spots, a portion of a surface such as a layer of a membrane or segments of a surface such as on a wire or tube. The immobilization oligonucleotides can be commingled or they may be attached to discrete locations on the support, such as different spots, different portions of a membrane or different regions of a wire or tube. These discrete locations may be immediately adjoining one another or at distal locations (to different degrees) depending on the designed flow of the assay and configuration of the assay apparatus, device or instrument. Alternatively, each of the oligonucleotides may be bound to different supports. For example, the immobilization oligonucleotides may be bound to different particles, different wires, different layers of a membrane, different individual pads of an array, different chambers in a device or different fibers.

The different supports can also be different types of solid supports. For example, the first oligonucleotide may be bound to the walls of a chamber and the second oligonucleotide can be bound to a fiber mesh within the interior portion of the chamber. Alternatively, the two different supports could be for example a membrane and a surface, a tube and a well, or a tube and a wire.

The different solid supports may be interspersed with one another, such as a mixture of suspended particles, a matrix of fibers or a bundle of wires. They can also be in discrete locations, such as a static bead array, individual pads of an array, different layers of a membrane, or different chambers in a device, such as in a microfluidic device.

Further, the different solid supports may be configured to be immediately adjoining one another or at distal locations (to different degrees) depending on the designed flow of the assay and configuration of the assay apparatus, device or instrument. A wide variety of solid supports types can be used in the present invention, including but not limited to, a porous or non-porous particle, fiber, membrane, wire, mesh, tube, chamber, well and flow cell. The scale of the support may vary in range from macro to micro to nano or smaller.

This method may further comprise additional steps that increase the number of desired RNA transcripts. The RNA transcripts produced above may then be annealed to the second immobilization oligonucleotide, which is then extended using polymerase to produce additional second cDNA strands. The RNA strand of the resulting RNA:DNA duplex is degraded using RNaseH and the first primer is hybridized to these additional second cDNA strands. The first primer and the additional second cDNA strands are extended to produce a duplex with an active T7 RNA polymerase promoter and more RNA transcripts are produced using a T7 RNA polymerase. These additional RNA transcripts in solution are annealed to the second immobilization oligonucleotide and the cycle is repeated.

In the embodiment described above, the sequence of the first immobilization oligonucleotide can be designed to hybridize to the target(s) of interest with high or low specificity or at a particularly desired level of specificity. This allows for very specific capture of a single target sequence or a generic nonspecific capture of all/most/many nucleic acids present in the sample. Likewise, the first primer and the second immobilization oligonucleotide can also be designed to bind with any level of desired specificity. For example, the sequence of the first primer and the two oligonucleotides can be designed to be exactly complementary to very particular regions of the target nucleic acid of interest, resulting in a high level of specificity (under the appropriate binding conditions). Additionally, the sequence of one or more of the oligonucleotides can be designed to discriminate between sequences containing only one or a few differences (e.g. a SNP, a point mutation, or more than one SNP or point mutation). One method to discriminate SNPs or point mutations is to design one or both of the primers to have the site of the SNP/mutation at the 3'-terminus. A correct match will allow extension and amplification whereas a mismatch will not.

The oligonucleotides may also be designed to straddle a junction site of a chimeric target, such as an mRNA target that is the product of a genetic translocation event (e.g. BCR/abl in Chronic Myelogenous Leukemia) or other fusion event (e.g. T2:ERG in prostate cancer). Alternatively, the sequence of any of the oligonucleotides can be designed to bind to multiple regions of the target with moderate specificity.

In a second embodiment of the aspect described above, a displacer oligonucleotide may also hybridize to the target nucleic acid at a location that is 3' of the first primer. When the first primer is extended, the displacer is also extended, displacing the extension product of the first primer from the target nucleic acid. One advantage of this approach is that thermal denaturation is not required to remove the extension product from the target nucleic acid, for example, if the target is DNA, digestion with RNaseH would not be considered. Furthermore, the extension product of the displacer may also enter the amplification process, thus increasing amplification yield. Additionally, a blocker oligonucleotide may also hybridize to the target nucleic acid. The blocker binds to the target nucleic acid at a location to the 5' side of the primer. The blocker arrests extension of the primer (as well as the displacer, if used), thus defining the length of the extension product(s). This technique of employing displacer and/or blocker oligonucleotides may also be utilized in other methods of the present invention.

In a third embodiment, the sequence of the oligonucleotides may comprise degenerate bases and/or regions of random bases, or may consist of random bases in its entirety, thus yielding low specificity. The method described herein yields an improvement over other existing methods in regards to control of assay specificity, in that the specificity can be modulated using the first and second immobilization oligonucleotides and the first primer in a manner described above. For example, designing first and second immobilization oligonucleotides and the first primer to hybridize the target nucleic acid with high specificity can achieve exquisite specificity. Correspondingly, the binding of the target nucleic acid to the first immobilization oligonucleotide can be performed under conditions of lower specificity. This allows multiple target types to be captured including wild type and mutant sequences, whereas the extension of the second immobilization oligonucleotide can be performed under higher specificity. This allows for the detection of SNPs or point mutations (see above). Under these conditions, the specificity of the first primer may be adjusted to deliver the desired overall level of specificity.

In a fourth embodiment, a set of four different second immobilization oligonucleotides are designed, each equipped with a different nucleotide (A, C, G or T) at the 3'-terminus. Each being specific for a different SNP in the corresponding position of the target nucleic acid(s). In one configuration, these four different second immobilization oligonucleotides may be bound to a solid support surrounding the first immobilization oligonucleotide. After capture of the target nucleic acids of interest using the first immobilization oligonucleotide and production of the first strand cDNA, re-capture of the cDNA with the second immobilization oligonucleotide and specific extension (i.e. matched 3'-terminus will extend and mismatched will not), all 4 possible SNPs can be identified in one assay.

In a fifth embodiment, the T7 promoter may be replaced with a variety of promoters, such as SP6 and T3. If this is done, the appropriate enzyme corresponding to the promoter is used for extension.

In a sixth embodiment, the first primer may further comprise a tag region wherein other elements may be included that provide a desired functionality. Examples of such elements include but are not limited to, for example, adapters, sequencing primers, amplification primers, additional capture elements, detection elements, mass tags, barcodes and binding elements. These elements are incorporated into amplification products. Furthermore, the second immobilization oligonucleotide may also comprise a tag region that is located 5' of the target nucleic acid binding region and may also comprise other elements that add desired functionality, examples of which are included immediately above.

Figure 2:
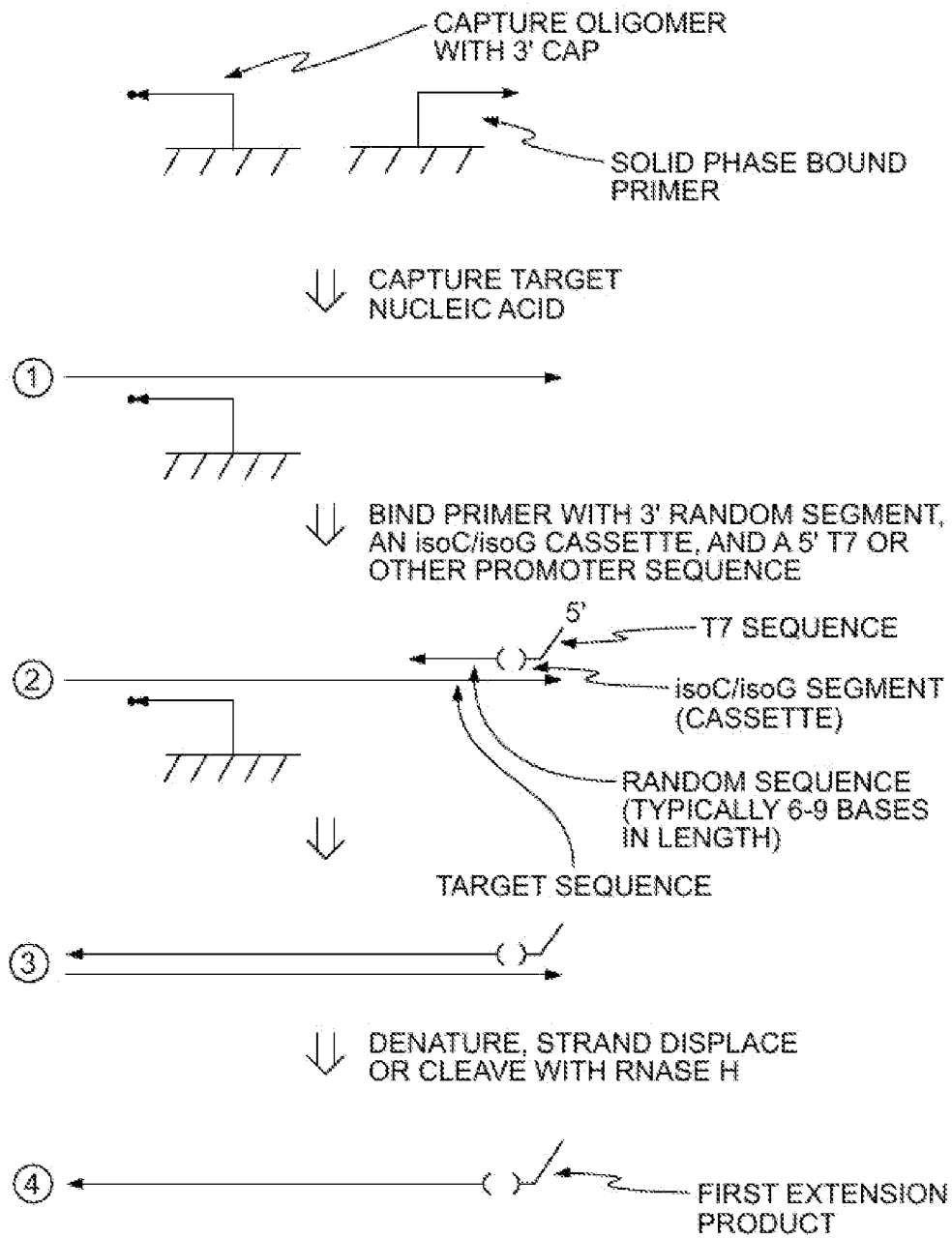
FIG. 2: is a schematic diagram of another method of the present invention utilizing a primer containing non-natural nucleotides to increase selectivity and decrease amplification of undesired nucleic acid sequences.
Figure 2:
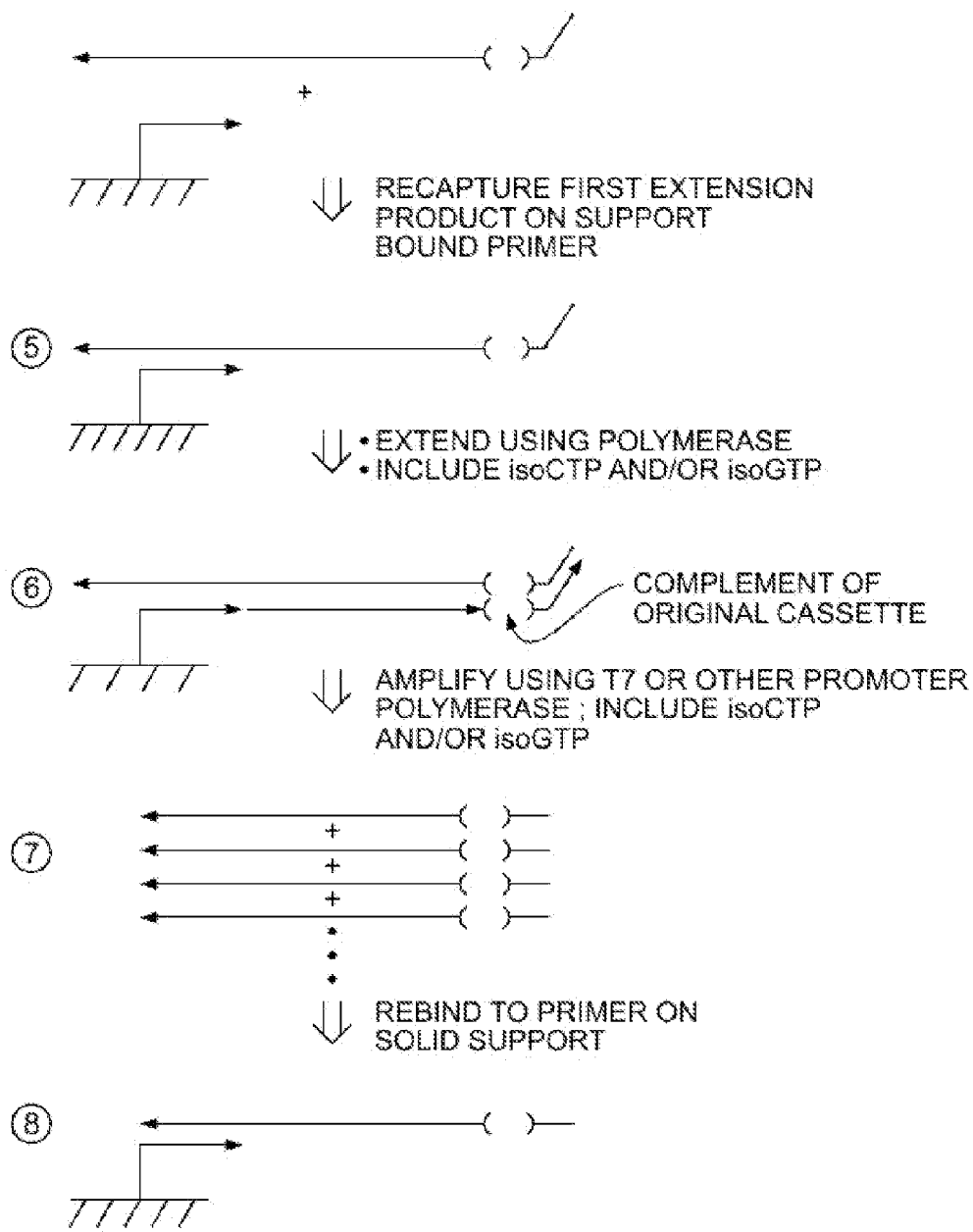
Figure 2:
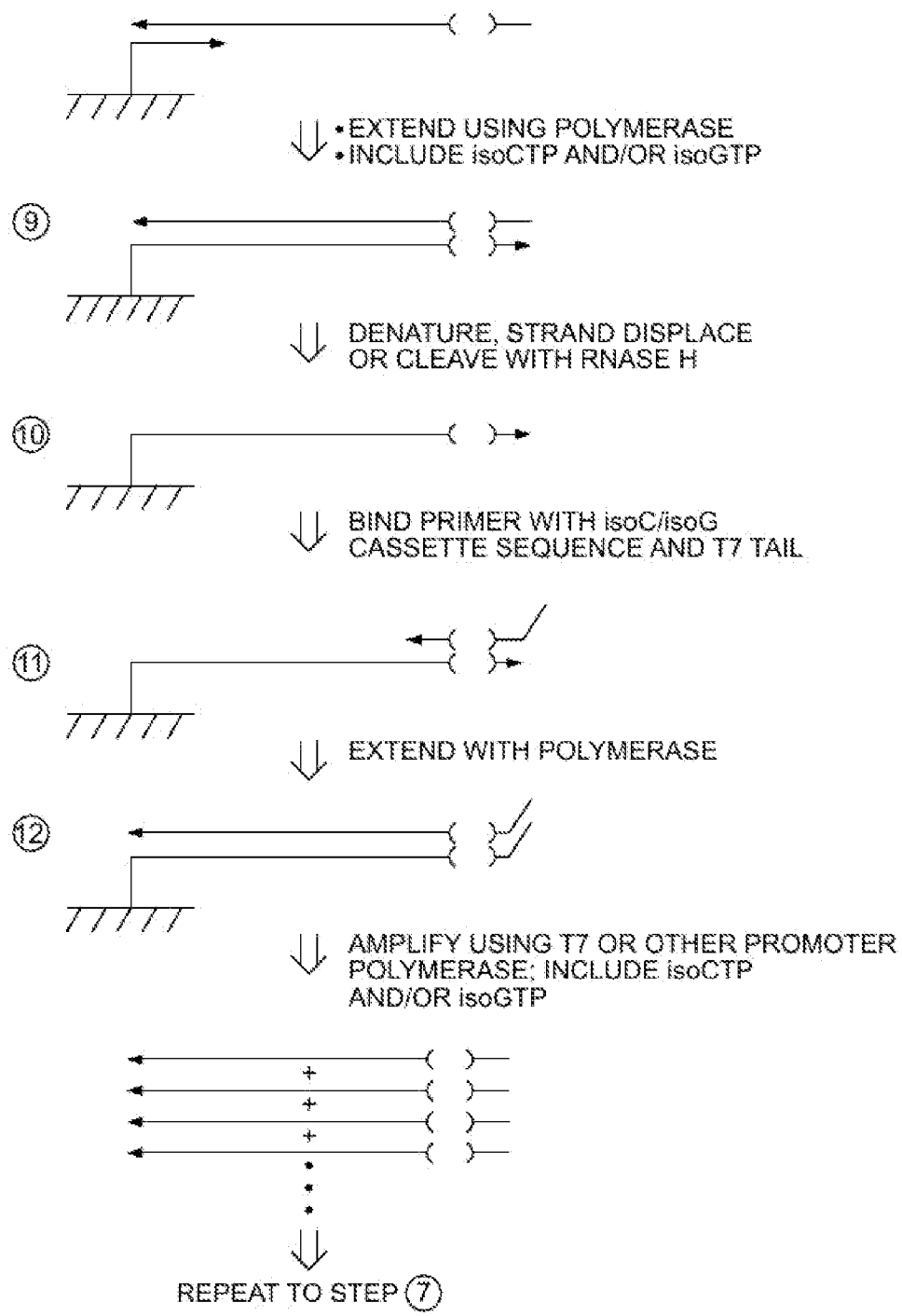

The tag region of the first primer may further comprise non-natural nucleotides, such as isocytosine (isoC) and isoguanine (isoG) (FIG. 2). These non-natural nucleotides will bind with isoG and isoC, respectively, but not with the natural nucleotides (A, C, G and T). These non-natural nucleotides may be covalently linked by standard phosphodiester bonds or other linkages, such as for example, phosphorothioate and methylphosphonate linkages. Using a first primer with this configuration produces a first cDNA containing isoC and/or isoG nucleotides, which is then used to produce RNA transcripts that also contain these isoC and/or isoG nucleotides. In the next round(s) of amplification, a second primer comprising a priming region that binds to the sequence generated from the first primer is utilized. This priming region contains isoC and/or isoG nucleotides that are complementary to the isoC and/or isoG nucleotides generated in the first round of amplification. The amplification then proceeds as described above, but now driven by the second primer. One advantage of this aspect is that the second primer is very specific for the isoC and/or isoG nucleotides and will not bind to other regions of the target(s), thus decreasing amplification side products. Other non-natural nucleotide pairs may be utilized, provided they pair with each other but not with the natural nucleotides (A, C, G and T) and are substrates for a DNA and/or RNA polymerase. Examples non-natural nucleotides include but are not limited to 6-amino-5-nitro-3-(10-β-D-20-deoxyribofuranosyl)-2(1H)-pyridone (also known as Z) and 2-amino-8-(10-β-D-20-deoxyribofuranosyl)-imidazo[1,2-a]-1,3,5-triazin-4(8H)-one) (also known as P) (Steven A. Benner, J. Am. Chem. Soc. 2011, 133, 15105-15112), 2,4-Diamino-5-(3-D-ribofuranosyl)pyrimidine (pyDAD) and 2'-deoxyxanthosine (puADA) (U.S. Pat. No. 8,354,225 B1) and pyridin-2-one and 2-amino-6-(2-thienyl)purine (Lee and Berdis, Biochim Biophys Acta, 2010 May; 1804(5): 1064-1080).

Figure 6:
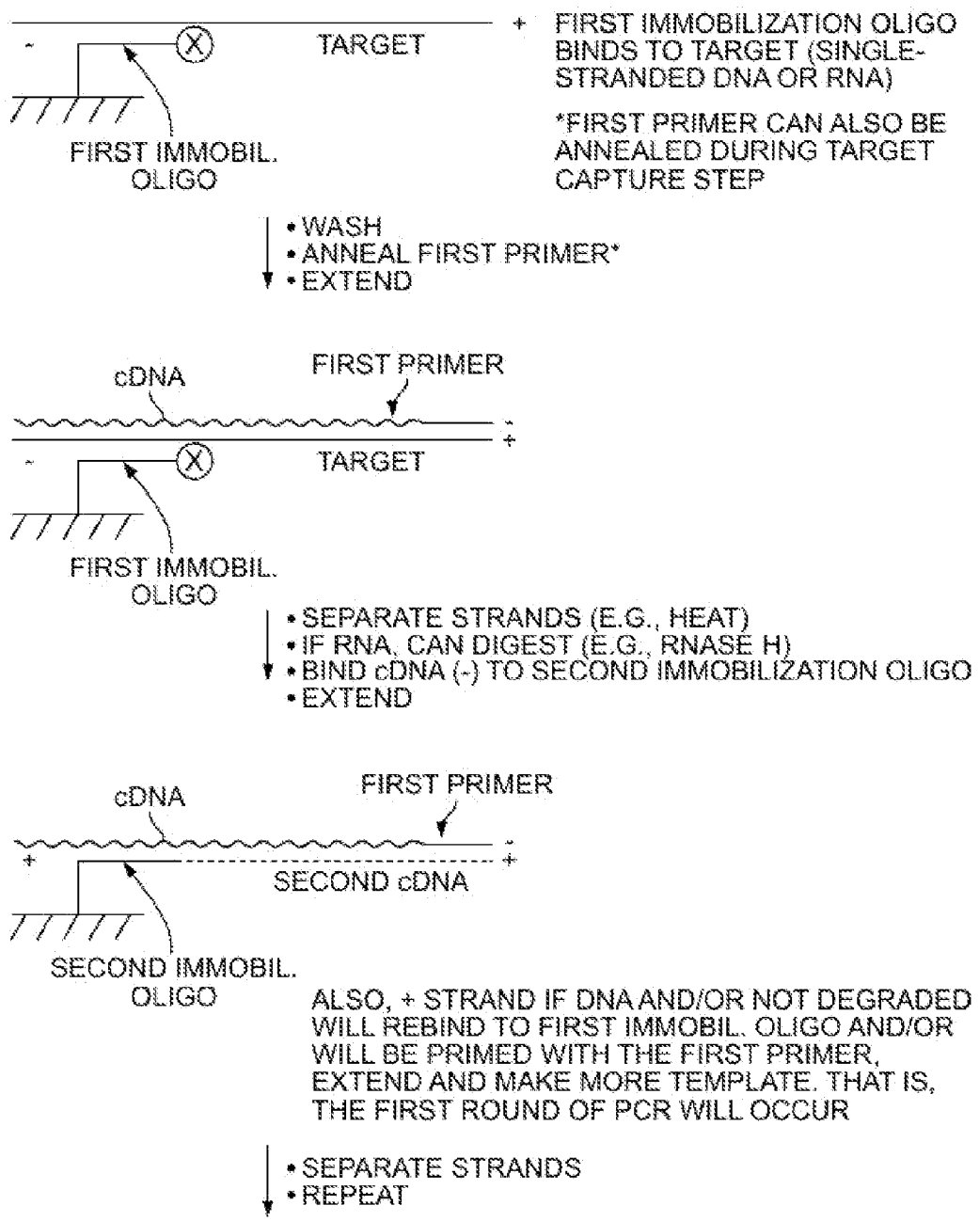
FIG. 6: is a schematic diagram of another method of the present invention that incorporates PCR.

A second aspect of the present invention, shown in FIG. 6, provides first and second immobilization oligonucleotides bound to either the same or adjacent regions of a solid support or to different supports. The sequence of the first immobilization oligonucleotide is complementary to a first portion of the target sequence. The sequence of the second immobilization oligonucleotide is the same as a second portion of the target sequence. The 3'-terminus of the first immobilization oligonucleotide is blocked in a manner preventing extension whereas the 3'-terminus of the second immobilization oligonucleotide allows extension.

The first portion and second portion of the target nucleic acid sequence may be the same or different. Under the majority of circumstances, it is preferable that the first and second immobilization oligonucleotide sequences are not exactly complementary.

The amplification method may be performed with RNA or DNA target nucleic acids. In one example, an RNA target (e.g., mRNA) from a sample is immobilized onto the solid support by hybridization to the first immobilization oligonucleotide. This may be a first solid support if the first and second immobilization oligonucleotides are bound to different supports. The solid support is washed to remove unbound components of the sample.

A first primer comprising a target-binding region is hybridized to the immobilized target RNA. The first primer is extended by polymerase to produce a first cDNA strand bound to a segment of the immobilized target RNA. The segment of RNA target is enzymatically degraded (e.g. RNaseH), leaving the first cDNA strand free in solution. The first cDNA strand is annealed to the second immobilization oligonucleotide on the first solid support, or on a second solid support if the first and second immobilization oligonucleotides are bound to different supports. The second immobilization oligonucleotide is extended using polymerase to produce a second cDNA strand bound to a segment of the first cDNA strand. The first primer and/or the second immobilization oligonucleotide(s) may further comprise a tag sequence(s).

Duplex strands are then separated (e.g. thermal denaturation). The first primer is hybridized to the second cDNA strand bound to the solid support and the first cDNA strand is hybridized to the second immobilization oligonucleotide. Furthermore, the original target strand hybridizes to the first immobilization oligonucleotide and the first primer hybridizes to the original target strand. The first primer and the second immobilization oligonucleotide are extended by polymerase and the process is repeated. This cycle is may be repeated to produced the desired amplification. It will be recognized by those skilled in the art that alternate work flows can be utilized in this embodiment of the invention. For example, the first primer may be bound to the target nucleic acid in the same step the target nucleic acid is bound to the first immobilization oligonucleotide. Also, the original target strand and the first cDNA strand can be separated using a method other than RNAse H digestion, such as heat denaturation.

Figure 7:
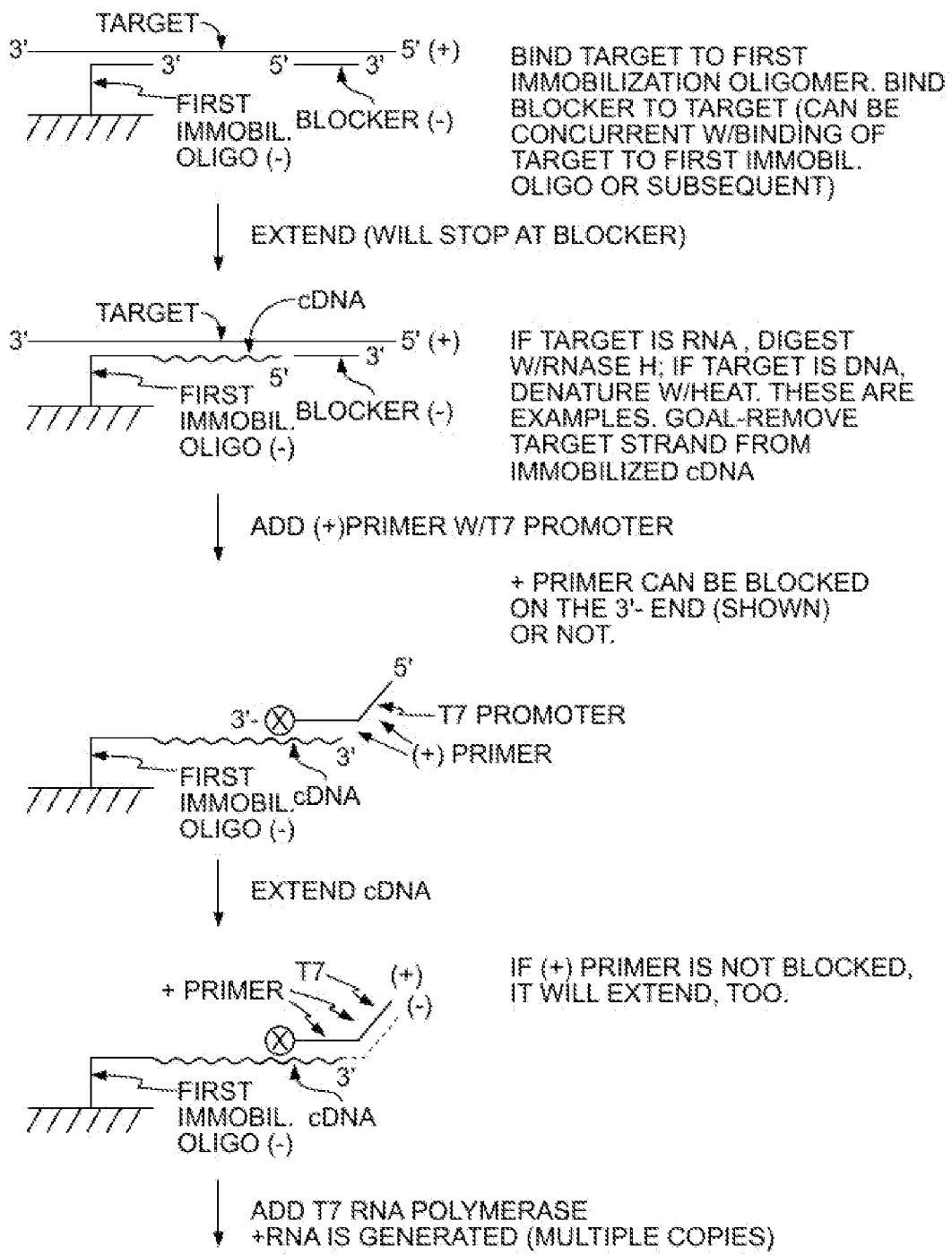
FIG. 7: is a schematic diagram of another method of the present invention wherein the first immobilization oligonucleotide and blocker oligonucleotide are bound to the target nucleic acid concurrently at the initiation of the method.
Figure 7:
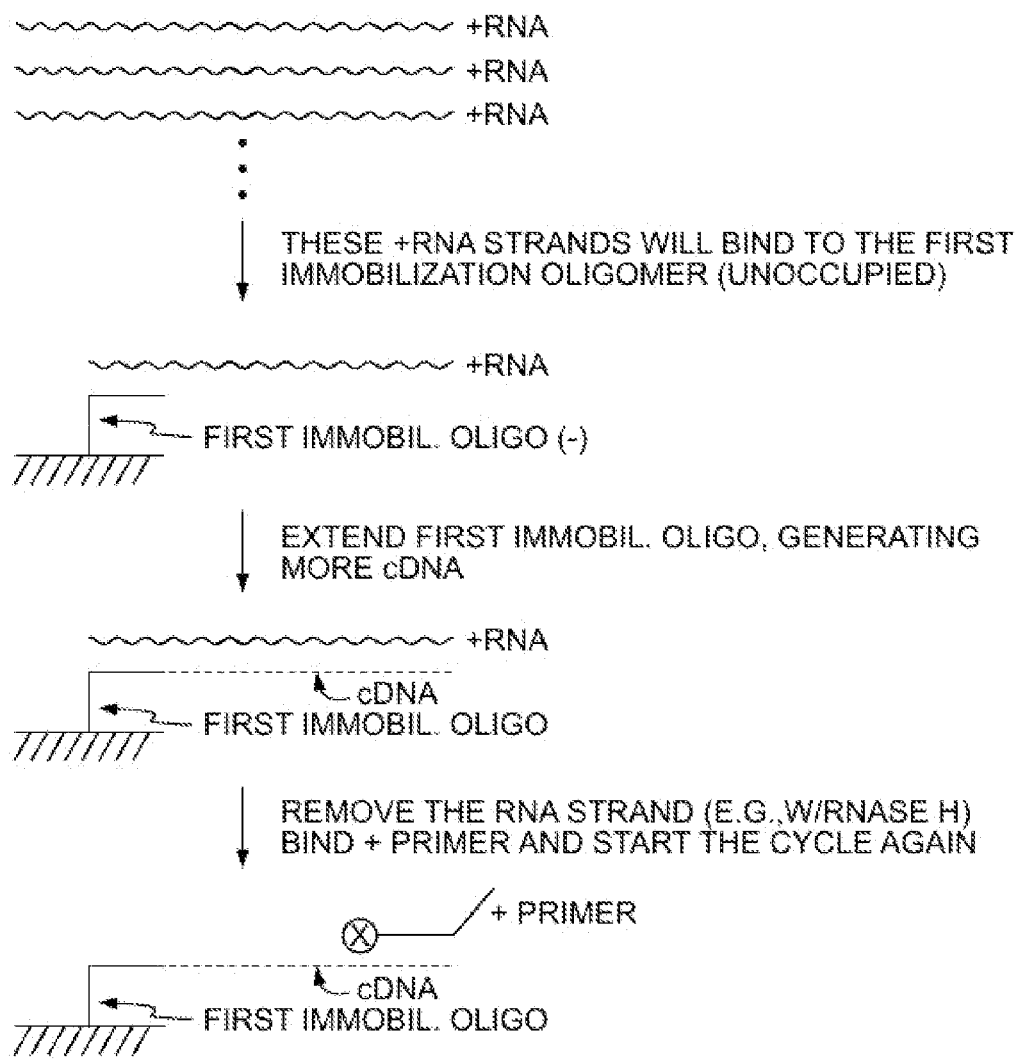

In a third aspect of the invention, shown in FIG. 7, an immobilization oligonucleotide/primer is hybridized to a solid support. The sequence of the immobilization oligonucleotide/first primer is complementary to a first portion of the target sequence. In one example of this embodiment, a blocker oligonucleotide complementary to a second portion of the target to the 5' side of the first portion of the target is also optionally provided. The blocker oligonucleotide is hybridized to the nucleic acid target and the nucleic acid target is hybridized to the immobilization oligonucleotide/first primer on the solid support.

The solid support is washed to remove unbound components of the sample. The immobilization oligonucleotide/first primer is extended with polymerase, and extension terminates at the blocker, to produce a first duplex nucleic acid of defined length bound to the solid support. The target nucleic acid is removed from the first duplex (e.g., digestion with RNaseH if the target is RNA or thermal denaturation), leaving a first nucleic acid bound to the solid support. A second primer comprising a binding region and a tag region, the tag region comprising a polymerase promoter sequence (e.g. T7 RNA polymerase promoter sequence), and, optionally, a 3'-terminus that is blocked in a manner preventing extension, is hybridized to the first nucleic acid such that the binding region overlaps the 3'-terminus of the first nucleic acid.

The first nucleic acid is extended to produce a second duplex nucleic acid that includes an active double stranded T7 RNA polymerase promoter site. Multiple RNA transcripts are then generated in solution from this duplex using a T7 RNA polymerase. These RNA transcripts may be hybridized to the immobilization oligonucleotide/primer on the solid support and the immobilization oligonucleotide/primer is extended by polymerase to produce a third duplex nucleic acid. The RNA strand of the third duplex is removed (e.g. RNaseH digestion, thermal denaturation) leaving a third nucleic acid bound to the solid support. The second primer is then hybridized to the third nucleic acid and the cycle is repeated until the desired amplification is achieved.

Figure 3:
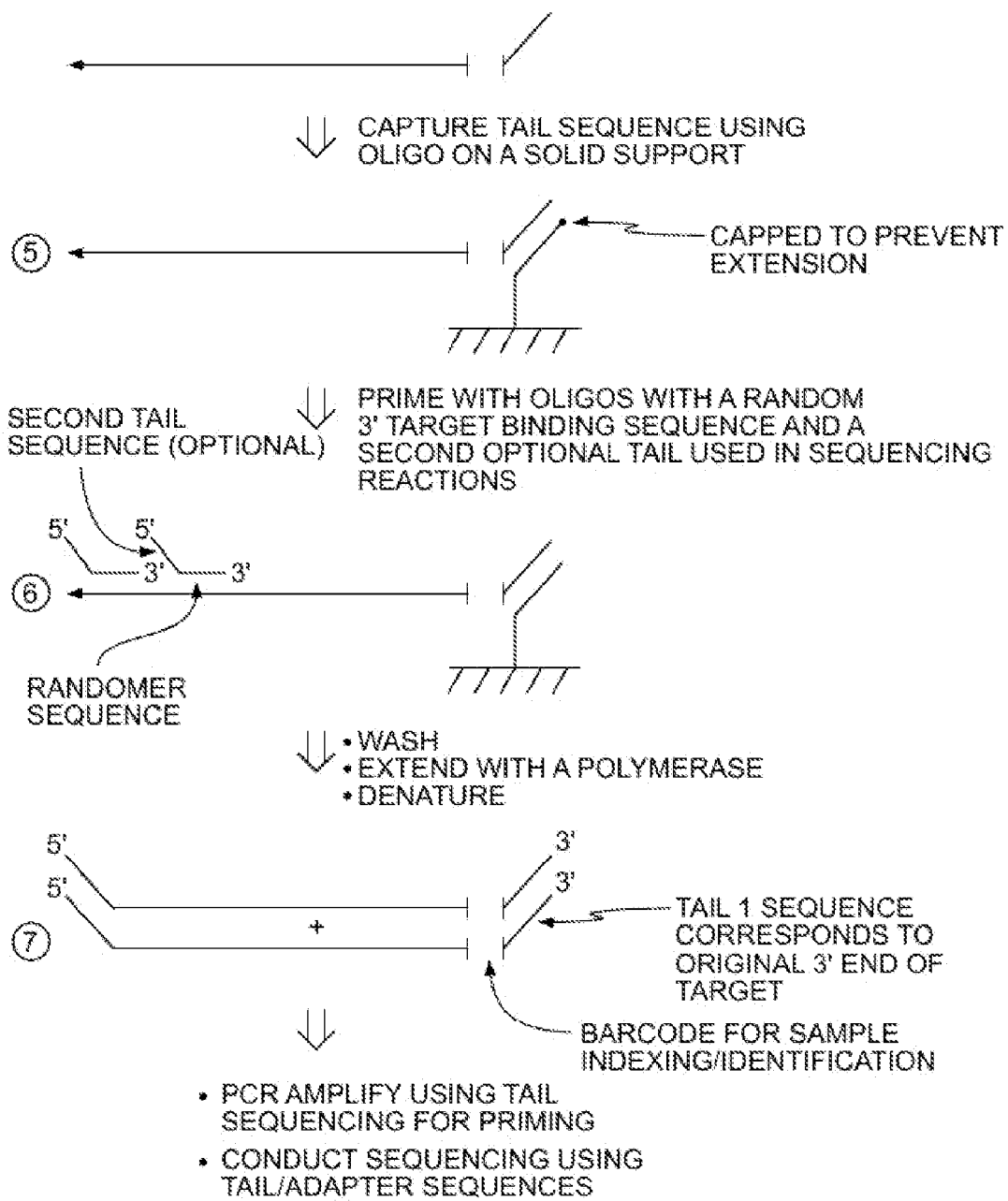
FIG. 3: is a schematic diagram of another method of the present invention utilizing a primer with a tag sequence to establish the orientation of the target oligonucleotide after amplification.
Figure 3:
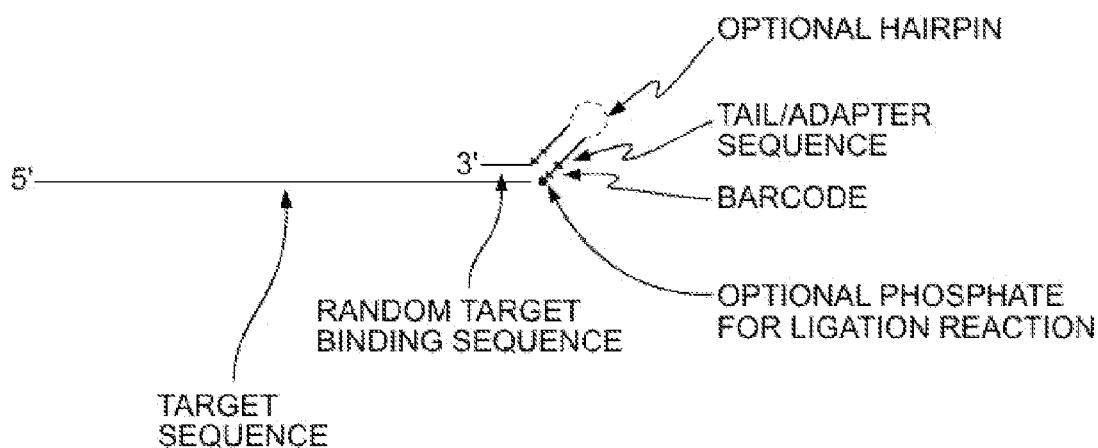

In a fourth aspect, a method is provided for determining the orientation of nucleic acid targets amplified from a fragmented sample, such as fresh frozen or formalin fixed paraffin-embedded tissue samples, to simplify sequencing (FIG. 3).

In one example, a nucleic acid from a fresh-frozen or formalin-fixed, paraffin-embedded (FFPE) tissue, biological fluid or other similar sample is fragmented producing a variety of nucleic acids. Initial capture of the target nucleic acid may occur prior to or after hybridization to the first primer. In addition, capture may be hybridization based or driven by ionic or other binding interactions (such as nucleic acid condensation or crowding methods). Optionally, capture may utilize a hairpin primer. In general, the capture is directed to the 5'-terminus of the target nucleic acid or is based on weak interactions along the length of the target nucleic acid sequence so that capture does not interfere with extension of the first primer or hairpin primer. Alternatively, the target/first primer complex is released from the solid support following removal of excess first primer.

If not previously bound, the first primer or hairpin primer is hybridized to the target nucleic acid. The first primer comprises a random, or largely random, about 6 to about 9 nucleotide segment on its 3'-terminus and a tag sequence on its 5'-terminus. A barcode sequence may be optionally included in the tag sequence, typically inserted between the 3'-random sequence and the remainder of the tag sequence. It is this tag sequence cassette, or the barcode sequence (if included) or a combination of the two that are used to determine the orientation of the initial mRNA target sequence. If the primer is a hairpin primer it will comprise an over-hanging 3'-random about 6 to about 9 nucleotide region that hybridizes preferentially to the 3'-terminus of the target nucleic acid sequence resulting from favorable end-stacking interactions. Alternatively, the hairpin may be ligated to the 3'-terminus of the target sequence.

Once hybridization of the first primer or hairpin primer to the target nucleic acid is complete, the solid support is washed to remove excess primer and the primer is extended with an appropriate polymerase. Typically the polymerase is a reverse transcriptase in the case of mRNA targets, optionally lacking RNaseH activity. This generates one or a number of cDNA/mRNA complexes dependent upon hybridization location of the first primer on the target nucleic acid. More specifically, whether the primer hybridized to the 3'-terminus or at multiple locations along the length of the mRNA target.

The cDNA is separated from the mRNA target. This step may be accomplished by digestion with RNaseH. The free cDNAs are captured, typically using the same capture method that was used in a preceding step of the protocol, and hybridized to a second primer that is analogous to the first primer, although optionally may not contain barcode. The cDNA/second primer complex is washed to remove excess primer. The second primer is extended using an appropriate DNA polymerase. However, reverse transcriptase having DNA polymerase activity may also be used. The product of this extension (referred to here as the constructs) will have known tag sequences on both their 5'- and 3'-termini.

These constructs are then amplified using third and fourth primers that are identical in sequence to at least a segment of the original tag sequences for the first and second primers, respectively. These third and fourth primers may optionally also contain tag sequences located on their 5'-termini that contain desired functional elements that were not included in the tag sequences of the first and/or second primers. Optionally, species may be separated according to size anywhere in this method as appropriate and desired.

This method may also be utilized with DNA targets, wherein a DNA polymerase is used in place of an RNA polymerase and strands in DNA/DNA duplexes are separated by means other than RNA digestion, such as by heat denaturation. Additionally, the first and second primers may be modified with nucleotide analogs, such as 5-methyl-dC, 2,6-diaminopurine, C5 propynyl-dC and -dU, and 2'-F-modified nucleotides to improve their hybridization properties to the target sequences.

In a fifth aspect, a method is provided for preparing amplified target nucleic acids of defined length utilizing displacer and blocker oligonucleotides.

Figure 4:
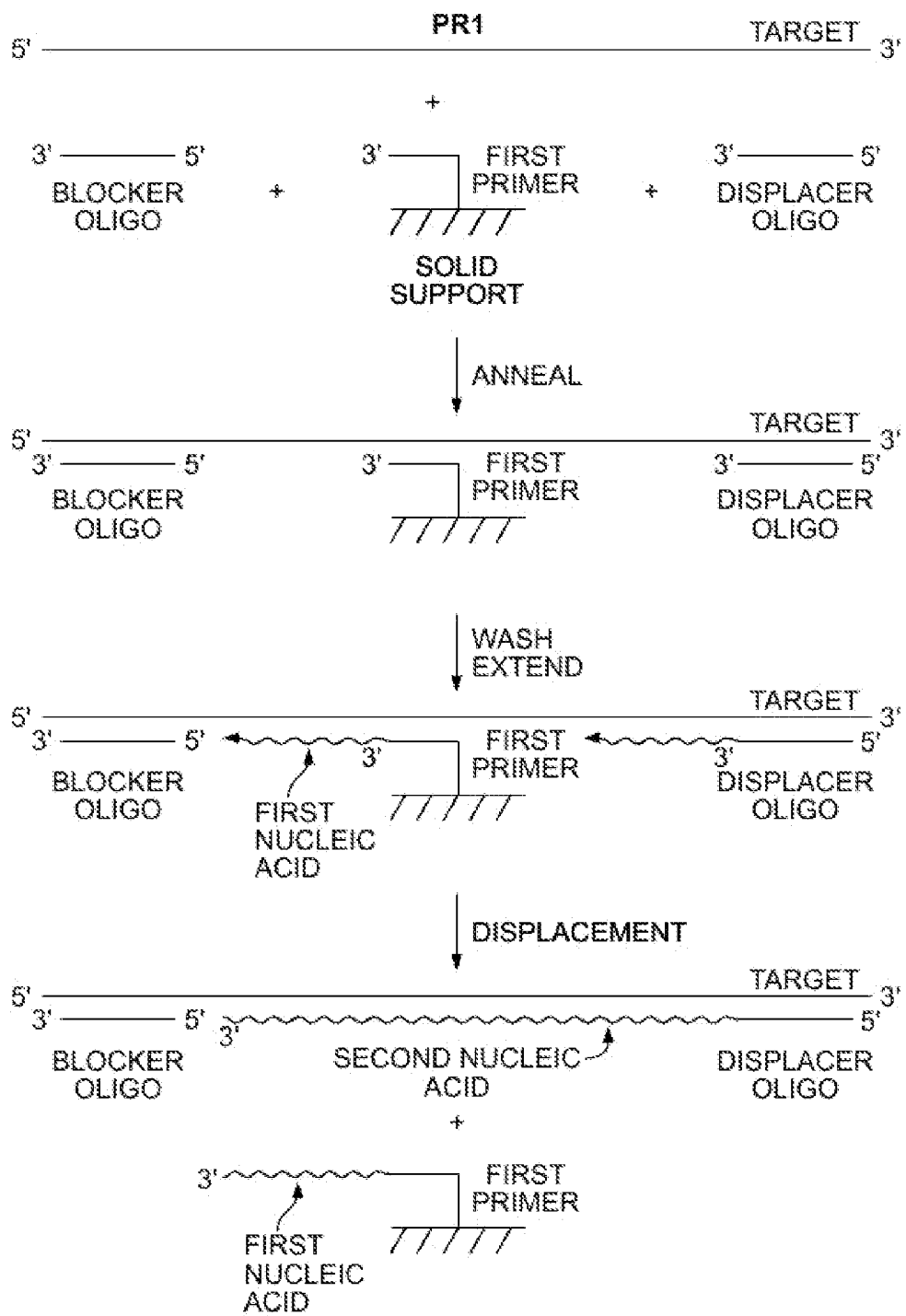
FIG. 4: is a schematic diagram of another method of the present invention utilizing blocker and displacer to prepare amplified nucleic acid target of defined length.
Figure 4:
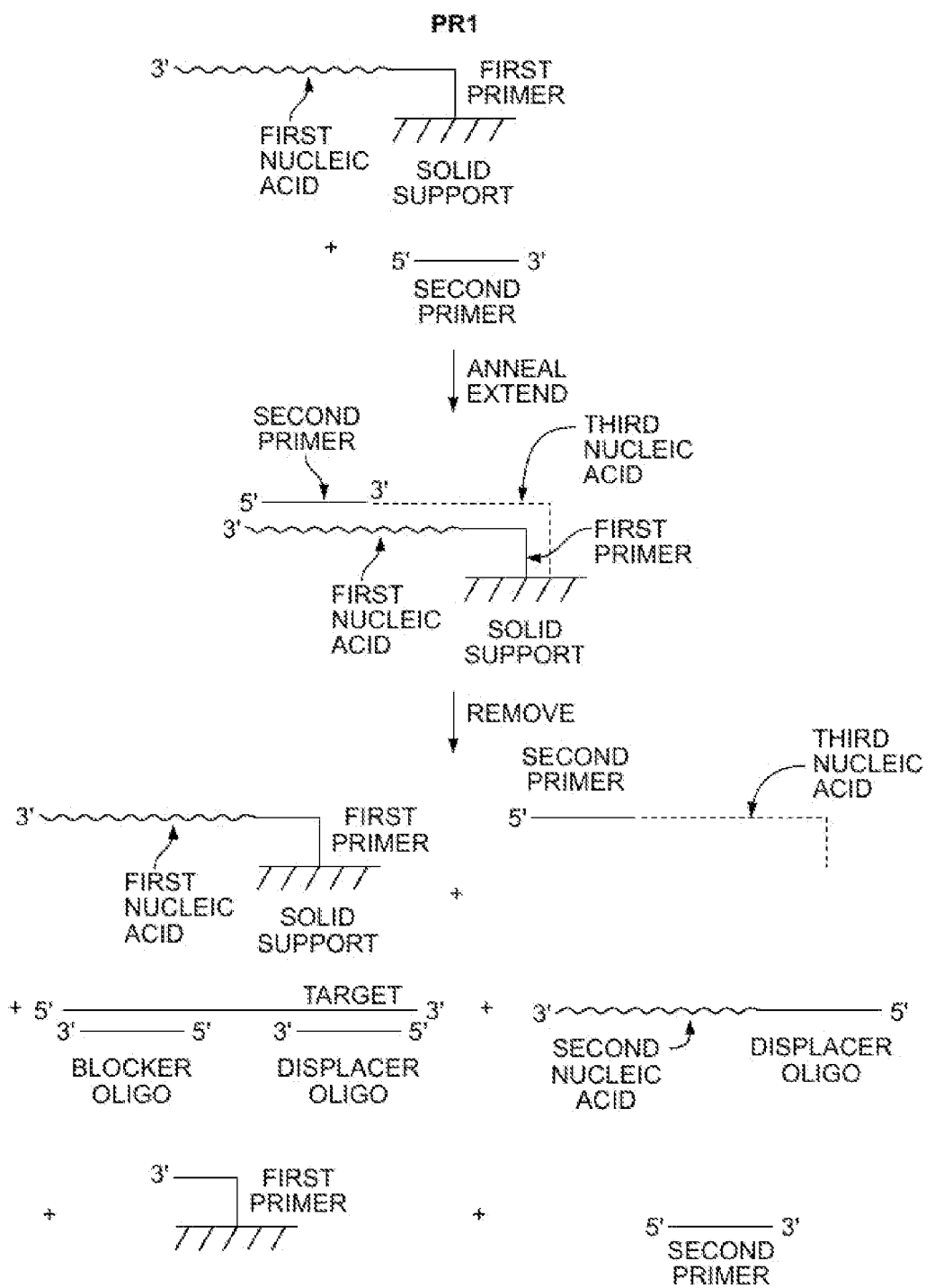

In one example, a first primer is immobilized on a solid support (FIG. 4). The sequence of the first primer is complementary to a first portion of a target nucleic acid sequence. A displacer oligonucleotide, blocker oligonucleotide and target nucleic acid are added to the solid support. The displacer sequence is complementary to a second portion of the target nucleic acid. The second portion being located to the 3' side of the first portion. The blocker sequence is complementary to a third portion of the target nucleic acid. The third portion is located to the 5' side of the first portion of the target. Both the displacer and blocker oligonucleotides are hybridized to the target nucleic acid and the hybridized target is immobilized onto the solid support by hybridization to the first primer.

The solid support is washed to remove unbound components of the sample as well as unbound blocker and displacer oligonucleotides. The first primer is extended by polymerase. Extension terminates at the blocker oligonucleotide, to produce a first duplex containing a first nucleic acid of defined length bound to the solid support. The displacer oligonucleotide is also extended by polymerase displacing the target nucleic acid from the first duplex. Extension terminates at the blocker oligonucleotide, to produce a second duplex containing a second nucleic acid of defined length that is not bound to the solid support.

A second primer is then hybridized to the first nucleic acid and extended by polymerase to produce a third duplex containing the first nucleic acid and a third nucleic acid. The second and third duplexes are then dissociated, e.g., heat denaturation or other appropriate means known in the art. The second primer is annealed to the first nucleic acid and extended by polymerase to produce more of the third duplex.

The third nucleic acid is immobilized onto the solid support by hybridization to unoccupied first primer. The first primer is extended by polymerase to produce more third duplex nucleic acid. The original target nucleic acid strand, with the displacer and blocker oligonucleotides bound thereto, is hybridized to unoccupied first primer and the first primer is extended by polymerase to produce more first duplex nucleic acid. The displacer oligonucleotide is also extended by polymerase displacing the target nucleic acid strand from the first duplex nucleic acid. Extension terminates at the blocker oligonucleotide, to produce a second duplex nucleic acid containing a second nucleic acid of defined length that is not bound to the support.

The second primer is hybridized to the second nucleic acid and extended by polymerase to produce a fourth duplex nucleic acid containing the second nucleic acid and a fourth nucleic acid. All duplexes are then denatured, and the cycle is repeated as desired.

In one embodiment of this example, additional blocker and/or displacer oligonucleotides are added to the reaction mixture described above after the washing step. Alternatively, blocker and displacer oligonucleotides are excluded in the first hybridization step with target but are added after the wash step.

In a second embodiment, the displacer and/or blocker oligonucleotides are omitted. If the displacer is omitted, strands of a duplex otherwise separated from one another via displacement activity are now separated by other means, such as heat denaturation.

In a third embodiment of this example, one or the other or both primers comprise a tag sequence. In one configuration, one or both of the tag sequences comprise an additional primer site that is a user-selected sequence. These one or two additional primer sequences can be utilized to drive amplification after the first round of amplification described above. Further, these one or two additional primers may be attached to a solid support or supports, either the same or different than the solid support to which the first primer described above is attached.

It is also contemplated that inclusion and potential use of tag sequences as described here in relation to a particular embodiment of the present invention may be applied to other embodiments of the present invention as well.

In a fourth embodiment, the first primer (bound to a solid support) has a sequence that supports immobilization of a number of target nucleic acids from the sample. For example, the sequence of the first primer can comprise a stretch of random nucleotides of about 6 to about 9 nucleotides in length that supports binding of many target nucleic acids (e.g. multiple fragments of a mRNA target). Alternatively, the sequence of the first primer may comprise a stretch of semi-random nucleotides of about 8 to about 20 nucleotides in length that support binding of a defined or semi-defined subset of a population of many target nucleic acids (e.g. multiple fragments from a genomic DNA target). Furthermore, some other level of specificity may be designed such that the majority of the target nucleic acids of interest in a sample can be immobilized. The primers are extended and the procedure continues as described above.

Figure 5:
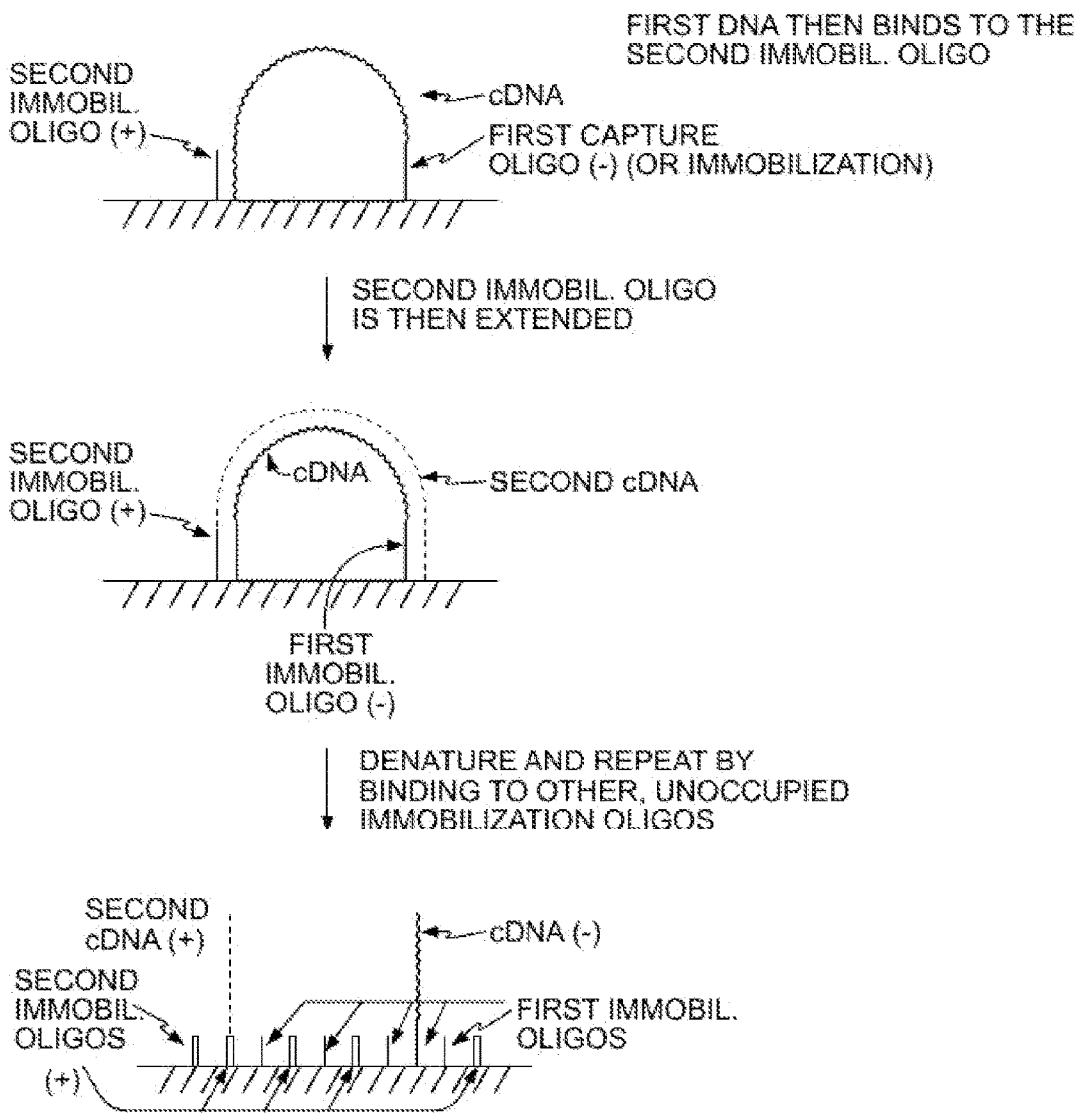
FIG. 5: is a schematic diagram of another method of the present invention utilizing first and second immobilization oligonucleotides that bind the first and second strand cDNAs of the target nucleic acid in a bridge configuration.

In a fifth embodiment, the method provides a first and second immobilization oligonucleotide/primer, both bound to a solid support (FIG. 5). The sequence of the first immobilization oligonucleotide/primer is complementary to a first portion of the target nucleic acid sequence. The sequence of the second immobilization oligonucleotide/primer is identical to a second portion of the target nucleic acid sequence. In one example, displacer and blocker oligonucleotides are utilized in the amplification method. The displacer oligonucleotide has a sequence that is complementary to a second portion of the target nucleic acid, wherein the second portion is located to the 3' side of the first portion of the target nucleic acid. The blocker oligonucleotide has a sequence complementary to a third portion of the target nucleic acid, wherein the third portion is located to the 5' side of the first portion of the target nucleic acid. The displacer and blocker oligonucleotides are hybridized to the target nucleic acid and the target nucleic acid is hybridized to the first immobilization oligonucleotide/primer on the solid support.

The solid support is washed to remove unbound components of the sample. The first immobilization oligonucleotide/primer is extended by polymerase. The extension terminates at the blocker oligonucleotide and a first duplex nucleic acid containing a first nucleic acid of defined length bound to the solid support is produced. The displacer oligonucleotide is also extended displacing the target nucleic acid from the first duplex nucleic acid as it is extended. Extension terminates at the blocker oligonucleotide and a second duplex nucleic acid containing a second nucleic acid of defined length is produced. This second duplex nucleic acid is not bound to the solid support. The second immobilization oligonucleotide/primer is hybridized to the first nucleic acid bound to the solid support to produce a bridge configuration (see FIG. 5).

The second immobilization oligonucleotide/primer is extended by polymerase to produce a third duplex nucleic acid containing the first nucleic acid and a third nucleic acid, both bound to the solid support. The second and third duplexes are then dissociated (e.g., via heat denaturation or other appropriate means known in the art). The first nucleic acid is hybridized to an unoccupied second immobilization oligonucleotide/primer and the second immobilization oligonucleotide/primer is extended by polymerase to produce more of the third duplex nucleic acid. Likewise, the third nucleic acid is hybridized to unoccupied first immobilization oligonucleotide/primer and the first immobilization oligonucleotide/primer is extended by polymerase to produce more third duplex nucleic acid. Furthermore, the second nucleic acid is hybridized to the second immobilization oligonucleotide/primer and second immobilization oligonucleotide/primer is extended to produce a fourth duplex nucleic acid.

The original target nucleic acid, with displacer and blocker oligonucleotides hybridized thereto, is hybridized to unoccupied immobilization oligonucleotide/first primer. The immobilization oligonucleotide/first primer is extended by polymerase to produce more first duplex nucleic acid. The displacer oligonucleotide is also extended, displacing the target nucleic acid from the first duplex as it is extended. Extension terminates at the blocker to produce a second duplex nucleic acid containing a second nucleic acid of defined length that is not bound to the solid support. All duplexes are then denatured, and the cycle is repeated as desired.

In a sixth embodiment, the target nucleic acid is double stranded. The first and second immobilization oligonucleotide/primers are complementary to a first region on the first and second strands of the double stranded target nucleic acid, respectively. These two regions are at different locations of the double stranded target nucleic acid. One or the other or both strands may also be provided optional displacer and/or blocker oligonucleotides as described above. The method for each strand is the same as described above for the first round of amplification, and then the bridge amplification as described above proceeds, with the displaced strands also entering the process, thus increasing amplification output. Target nucleic acids left in solution may also participate in further rounds of hybridizing the displacer and/or blocker and being bound to the primer on the support, and also participate in further amplification, again increasing the amplification output.

It is also contemplated that amplification of both strands of a double stranded target described here in relation to a particular embodiment of the present invention may be amplified in other embodiments of the present invention as well.

The information set forth above is provided to give those of ordinary skill in the art a complete disclosure and description of how to make and use the embodiments of the device and methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference. For example, many of the wash steps cited in the different methods are optional as are some of the steps that remove and/or separate two nucleic acid strands from one another. Not performing at least some of the wash and/or separation steps will afford a faster, simpler and more economical work flow, while still achieving the desired results. In another example, the stepwise addition/binding of certain oligonucleotides and/or target nucleic acids in the exemplified methods may be combined. In addition, the use of tag sequences is optional in some embodiments, and their potential composition may vary from those exemplified above but still within the scope of the knowledge of one skilled in the art. In some cases, the use of a blocking group to prevent exonuclease digestion from the 5'-terminus may not be required. Furthermore, a variety of polymerases, extension conditions and other amplification protocols known to those skilled in the art may be used in various steps or combination of steps in the methods described above. Other obvious modifications to the methods disclosed that would be obvious to those skilled in the art are also encompassed by this invention.

We claim:

1. A method of immobilizing and amplifying a target nucleic acid from a sample containing a mixture of nucleic acids, said method comprising the steps of:

applying said sample to a solid support, said solid support having a first oligonucleotide and a second oligonucleotide affixed thereto, wherein said first oligonucleotide is blocked to prevent extension from the 3'-terminus and has a sequence complementary to a first portion of said target nucleic acid and said second oligonucleotide has a sequence that is identical to a second portion of said target nucleic acid, wherein said target nucleic acid binds said first oligonucleotide and optionally washing said solid support to remove unbound nucleic acids;

hybridizing a primer to said target nucleic acid wherein said primer contains a target binding region and a polymerase promoter sequence and extending said primer by polymerase to produce a first duplex nucleic acid and optionally removing said target nucleic acid from said duplex nucleic acid to produce a first nucleic acid;

annealing said first nucleic acid to said second oligonucleotide and extending said second oligonucleotide by polymerase to produce a second duplex nucleic acid containing said first nucleic acid and a second nucleic acid; and generating multiple copies of a third nucleic acid by polymerase, thereby amplifying said target nucleic acid.

2. The method according to claim 1, further comprising the steps of:

annealing said amplified third nucleic acid with said second oligonucleotide and extending said second oligonucleotide to produce a third duplex nucleic acid;

optionally removing said amplified third nucleic acid to produce a solid support bound fourth nucleic acid;

annealing said primer sequence to said fourth nucleic acid and extending said primer and said fourth nucleic acid by polymerase to produce a fourth duplex nucleic acid containing a fifth nucleic acid and additional second nucleic acid; and generating multiple copies of said third nucleic acid by polymerase, said polymerase being specific to a promoter on said fourth duplex nucleic acid thereby amplifying said target nucleic acid.

3. The method according to claim 1, wherein said primer further comprises a tag sequence comprising one or more non-natural nucleotides.

4. The method according to claim 1, wherein said second oligonucleotide is four oligonucleotides each with a different nucleotide at the 3'-terminus specific for four different SNPs of said first nucleic acid.

* * * * *